US011000702B2

(12) United States Patent
Belley et al.

(10) Patent No.: US 11,000,702 B2
(45) Date of Patent: May 11, 2021

(54) SYSTEMS AND METHODS FOR THE VERIFICATION OF SOURCE PLACEMENT FOR BRACHYTHERAPY RADIATION PROCEDURES USING REAL TIME RADIATION DETECTORS

(71) Applicant: Duke University, Durham, NC (US)

(72) Inventors: Matthew D. Belley, Durham, NC (US); Michael J. Therien, Durham, NC (US); Ian N. Stanton, Durham, NC (US); Terry T. Yoshizumi, Hillsborough, NC (US); Brian W. Langloss, Durham, NC (US); Oana I. Craciunescu, Hillsborough, NC (US); Junzo P. Chino, Durham, NC (US)

(73) Assignee: Duke University, Durham, NC (US)

( * ) Notice: Subject to any disclaimer, the term of this patent is extended or adjusted under 35 U.S.C. 154(b) by 644 days.

(21) Appl. No.: 15/517,624

(22) PCT Filed: Oct. 9, 2015

(86) PCT No.: PCT/US2015/054831
§ 371 (c)(1),
(2) Date: Apr. 7, 2017

(87) PCT Pub. No.: WO2016/093942
PCT Pub. Date: Jun. 16, 2016

(65) Prior Publication Data
US 2017/0304652 A1 Oct. 26, 2017

Related U.S. Application Data

(60) Provisional application No. 62/061,860, filed on Oct. 9, 2014, provisional application No. 62/209,470, filed on Aug. 25, 2015.

(51) Int. Cl.
*A61N 5/10* (2006.01)

(52) U.S. Cl.
CPC ........ *A61N 5/1071* (2013.01); *A61N 5/1001* (2013.01); *A61N 5/1075* (2013.01); *A61N 2005/1076* (2013.01)

(58) Field of Classification Search
CPC .. A61N 5/1071; A61N 5/1075; A61N 5/1001; A61N 2005/1076
See application file for complete search history.

(56) References Cited

U.S. PATENT DOCUMENTS

2003/0163016 A1* 8/2003 Testardi ............... A61N 5/1048
600/2
2003/0212302 A1* 11/2003 Rozenfeld ............ A61N 5/1007
600/1

(Continued)

FOREIGN PATENT DOCUMENTS

DE 4143401 8/1993
WO WO 03/062855 7/2003

(Continued)

OTHER PUBLICATIONS

International Search Report and Written Opinion dated Jul. 1, 2016 of International Application No. PCT/US2015/054831 filed Oct. 9, 2015, 13 pages.

*Primary Examiner* — Kaylee R Wilson
(74) *Attorney, Agent, or Firm* — Polsinelli PC; Michelle L. McMullen; J. Wendy Davis

(57) ABSTRACT

The present disclosure provides systems and methods for verifying radiation source delivery in brachytherapy by allowing for the radiation source location and dwell time to be determined via real-time measurement. In an embodiment, a radiation detector may be disposed proximate to a radiotherapy target. The radiation detector is configured to provide real-time information indicative of ionizing radia- (Continued)

tion emitted by a radiation source. A controller may perform operations including receiving, from the radiation detector, real-time information indicative of at least one of: a particle flux rate, an energy fluence, or an absorbed dose of ionizing radiation emitted from the radiation source. The operations may also include determining, based on the received information, at least one of: a location of the radiation source or a dwell time of the radiation source.

27 Claims, 18 Drawing Sheets

(56) References Cited

U.S. PATENT DOCUMENTS

| | | | | |
|---|---|---|---|---|
| 2010/0152521 | A1* | 6/2010 | Price | A61N 5/1027 |
| | | | | 600/7 |
| 2010/0288934 | A1* | 11/2010 | Keppel | A61N 5/1071 |
| | | | | 250/362 |
| 2012/0068075 | A1* | 3/2012 | Beddar | G01T 1/023 |
| | | | | 250/362 |
| 2013/0320220 | A1* | 12/2013 | Donowsky | B32B 15/08 |
| | | | | 250/366 |

FOREIGN PATENT DOCUMENTS

| | | |
|---|---|---|
| WO | WO 2008/009917 | 1/2008 |
| WO | WO 2012/034157 | 3/2012 |
| WO | WO 2013/120795 | 8/2013 |

* cited by examiner

SYSTEMS AND METHODS FOR THE VERIFICATION OF SOURCE PLACEMENT FOR BRACHYTHERAPY RADIATION PROCEDURES USING REAL TIME RADIATION DETECTORS

CROSS-REFERENCE TO RELATED APPLICATION

The present application is a national stage entry of PCT/US15/54831 filed Oct. 9, 2015, which claims priority to U.S. Provisional Patent Application No. 62/061,860, filed Oct. 9, 2014 and U.S. Provisional Patent Application No. 62/209,470, filed Aug. 25, 2015, the contents of each of which are hereby incorporated by reference.

GOVERNMENT LICENSE RIGHTS

This invention was made with government support under Federal Grant Nos. NRC HQ-12-G-38-0022 and 2012-DN-077-ARI062 awarded by the U.S. NRC and DHA, respectively. The government has certain rights in the invention.

BACKGROUND

Brachytherapy involves the placement of a sealed radiation source inside or near a radiotherapy target. Brachytherapy is a common treatment for tumors, particularly cervical, prostate, breast, and skin cancers.

SUMMARY

In an aspect, a system is provided. The system includes a radiation detector and a controller. The radiation detector is located disposed proximate to a radiotherapy target. The radiation detector is configured to provide real-time information indicative of ionizing radiation emitted by a radiation source. The controller includes a memory and a processor. The memory stores instructions that are executable by the processor to cause the controller to perform operations. The operations include receiving, from the radiation detector, real-time information indicative of at least one of: a particle flux rate, an energy fluence, or an absorbed dose of ionizing radiation emitted from the radiation source. The operations also include determining, based on the received information, at least one of: a location of the radiation source or a dwell time of the radiation source.

In another aspect, a method is provided. The method includes positioning a radiation detector proximate to a radiotherapy target. The method also includes receiving, from a radiation detector, real-time information indicative of at least one of: a particle flux rate, an energy fluence, or an absorbed dose of ionizing radiation emitted from the radiation source. The method additionally includes determining, based on the received information, at least one of: a location of the radiation source or a dwell time of the radiation source.

In another aspect, a method is provided. The method includes determining a calibration function. The calibration function includes a calibration voltage as a function of a source-detector-distance (SDD) and a source activity. The calibration voltage includes a voltage provided by a radiation detector in response to receiving radiation emitted by a radiation source in a medium. The SDD includes a relative distance between the radiation source and the radiation detector. The source activity includes a number of radioactive decays per second. The method also includes determining, in real time, a location of the radiation source relative to a radiotherapy target based at least on: the calibration function, the source activity, and a real-time voltage received from the radiation detector. The method additionally includes determining, in real time, an absorbed dose based on the determined location of the radiation source relative to the radiotherapy target.

In another aspect, a method for delivering radiation therapy to a patient in need thereof is provided. The method includes positioning a radiation detector proximate to a radiotherapy target including in vivo tissue. The method also includes receiving, from a radiation detector, real-time information indicative of at least one of: a particle flux rate, an energy fluence, or an absorbed dose of ionizing radiation emitted from the radiation source. The method yet further includes determining, based on the received information, at least one of: a location of the radiation source or a dwell time of the radiation source.

Other aspects, embodiments, and implementations will become apparent to those of ordinary skill in the art by reading the following detailed description, with reference where appropriate to the accompanying drawings.

DETAILED DESCRIPTION

Figure 1:
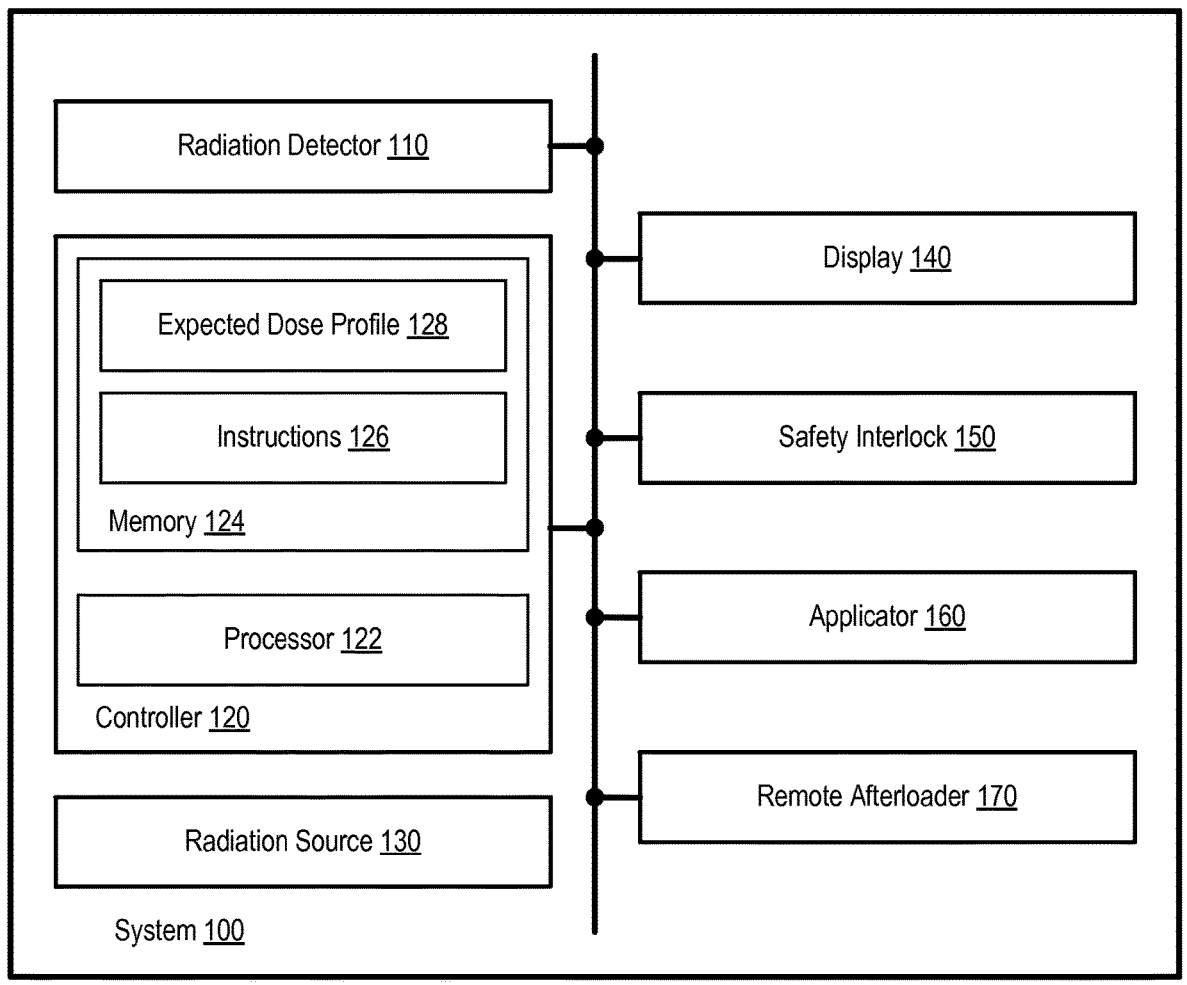
FIG. 1 illustrates a system, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where in vivo radiation dose information may be useful. The environment may include any living or non-living body or a portion thereof. The environment may include non-human tissues. For example, one of skill in the art will recognize that the embodiments disclosed herein may be applied generally in many different contexts to conduct localized radiation dosimetry. Moreover, while the present disclosure describes some embodiments for use in vivo, one of skill in the art will also recognize that in vitro and/or ex vivo applications are possible as well.

As used herein, the term "tumor" refers to a tissue sample or cells that exhibit a cancerous morphology, express cancer markers, or appear abnormal, or that have been removed from a patient having a clinical diagnosis of cancer. A tumorogenic tissue is not limited to any specific stage of cancer or cancer type, and expressly includes dysplasia, anaplasia and precancerous lesions such as inter alia ademona.

As used herein, the term "tissue" refers to patient tissue, and includes but is not limited to for example, epithelial tissue, tissue of the breast, prostate, cervix, uterus or other gynecologic tissue. Patient tissue may further include, but is not limited to tumorogenic or cancerous tissue. As used herein, the term "in vivo" refers to live or living cells, tissues, or systems. In vivo patient tissue is located inside the body (i.e., under the dermis), on an epithelial layer either inside (e.g., vaginal canal) or outside of the body. In vivo patient tissue may further include but is not limited to gynecological tissue in or on the vaginal canal/cervix, uterus, prostate tissue, or breast tissue below the outer dermis.

Overview

Current brachytherapy treatments do not make use of real-time radiation dose measurements to verify (i) source location and (ii) dwell time. Rather, treatments are delivered based on computer simulations and prior measurements performed ex vivo, which may involve computational human phantoms and/or tissue phantoms.

A lack of information about real-time radiation delivery may limit the ability of the nurse/physicist/physician to accurately deliver brachytherapy treatments. Furthermore, without real-time radiation dose information, treatment planning software may not be able to notify the user, and/or terminate the treatment in response to errors in source location and/or dwell time.

The present disclosure addresses these problems by describing systems and methods that provide real-time feedback to (i) the human operator and/or (ii) a controller, to allow for the in-vivo (a) verification of treatment delivery and to (b) provide an early indicator for termination of treatment when source positioning errors occur.

In an example embodiment, a real-time radiation detector may be used to measure and quantify a dose, a fluence, and/or other information indicative of ionizing radiation emitted from a radiation source during delivery of brachytherapy treatment to a radiotherapy target. In some cases, such information may be utilized, at least in part, to determine a spatial location of the radioactive source. Furthermore, such information may indicate a dwell time of the radioactive source.

The radiation detector may be located near or in the radiotherapy target. For example, the radiation detector may be inserted, implanted, or otherwise positioned in or near the radiotherapy target.

In an example embodiment, the radiotherapy target may include human cells, which may be precancerous or cancerous cells. Other types of radiotherapy targets are possible. In the case of a tumor, at least a portion of the radiation detector may be positioned inside the tumor so as to measure dose information at the radiotherapy target.

In an example embodiment, the radiation detector may be a fiber-optic scintillation detector. In such a scenario, at least a portion of the fiber-optic scintillation detector may be placed in vivo in a patient. In some embodiments, an optical fiber of the scintillation detector may be physically and/or optically coupled to a cylindrical stump so as to provide a fixed geometry reference, which may improve measurement confidence and/or repeatability. In such scenarios, the cylindrical stump may be part of an applicator configured to house the radiation source. Namely, the applicator may include a plurality of dwell positions at which the radiation source may dwell for respective dwell times during treatment. Additionally or alternatively the optical fiber of the scintillation detector may be located apart from the applicator. In some embodiments, multiple radiation detectors may be used so as to obtain more reliable information and/or three-dimensional dose information.

During treatment (e.g., while the radiation source is moved into the patient and along the various dwell positions in the stump), a real-time signal from the radiation detector may be recorded and/or monitored by a controller. The controller may be configured to analyze the signals from the radiation detector so as to determine, for example, the location of the radiation source within the patient and/or with respect to the radiation detector. The controller may be additionally or alternatively configured to determine the dwell time of the radiation source at a given dwell location in the stump.

Such location and/or dwell time information may be utilized in a quality assurance (QA) process and/or verification of the brachytherapy procedure. In some embodiments, the information obtained by the controller may be combined with a priori knowledge of the radiation source (e.g., composition, size, weight, emission pattern, etc.) and/or patient anatomy so as to determine an overall dose distribution within the patient. In such scenarios, a "baseline" dataset may be estimated, calculated, derived from theory, obtained via phantom, or otherwise determined so as to form a planned treatment template. The planned treatment template may include an expected signal level from the radiation detector. The expected signal level may be representative of the signal that should be obtained during the actual treatment delivery.

In some embodiments, the controller may be operable to determine a safety interlock condition in response to a deviation of the measured location or dwell time compared to the respective expected signal level. In response to determining the safety interlock condition, the controller may cause a safety interlock to withdraw the radiation source, close an aperture, or otherwise terminate the brachytherapy treatment delivery to the patient.

In an example embodiment, the system may include a display and the controller may be configured to display information about the expected detector signal and the real-time detector signal via the display. For example, the controller may cause the display to show the expected detector signal as a "baseline" measurement. Furthermore, the controller may cause the display to overlay or otherwise show the real-time data during treatment to ensure that the radiation source location is accurate and at the planned positions.

The real-time display of the expected signal and the measured signal may be displayed to the user operating a treatment planning system to provide better quality assurance and safety. For example, the display may be incorporated directly into a treatment planning system monitor, which may be viewed by the nurse/physicist/physician during the treatment procedure.

In some embodiments, the systems and methods disclosed herein may be used in conjunction with a remote afterloading system. The remote afterloading system may be configured to house and deliver one or more radiation sources so as to provide a dose of ionizing radiation to a patient. The remote afterloading system may include a shielded safe configured to store the radiation source(s). Furthermore, the remote afterloading system may be configured to move the radiation source(s) to various dwell positions along the applicator as described above. Yet further, the remote afterloading system may be configured to withdraw the radiation source and/or the applicator in response to receiving information indicative of a safety interlock condition (e.g., as determined by the controller as described herein).

The controller may include a computer having a processor and a memory. The controller may take other forms as well. For example, the controller may include a distributed computing system or a cloud-based server network. Alternatively or additionally, the controller may be a mobile device. The controller may include software, such as hardware drivers and/or application programming interfaces, configured to control the aforementioned elements of the system. The controller may communicate with and/or control some or all of the other elements of the system using wireless communications.

System Examples

FIG. 1 illustrates a system 100, according to an example embodiment. The system 100 includes a radiation detector 110, a controller 120, and at least one radiation source 130. The system 100 may also include one or more displays 140, a safety interlock 150, an applicator 160, and/or a remote afterloader 170.

The radiation detector 110 may be configured to provide real-time information indicative of ionizing radiation emitted by a radiation source. In an example embodiment, the radiation detector 110 may include a fiber optic scintillation detector. The fiber optic scintillation detector may include a scintillation material operable to provide a characteristic optical response (e.g., fluorescence light) in response to absorbing energy associated with a radioactive decay process. The scintillation material may be physically and optically coupled to a terminus of the optical fiber. In an example embodiment, the scintillation material may include a cerium-activated lithium silicate or boron silicate glass. In an example embodiment, the scintillation material may include an inorganic crystal with an activator impurity. For example, an alkali metal halide (e.g., NaI CsI, or KI) may be doped with thallium (NaI(Tl), CsI(Tl), or KI(Tl)) to form a scintillator material. In yet other example embodiments, the scintillation material may be a "plastic scintillator", which may include a fluorophore suspended in a solid polymer matrix. For instance, the scintillation material may include polyethylene naphthalate. Other scintillation materials are possible. In an example embodiment, the scintillation material may be configured to emit emission light at a wavelength of 611 nm when exposed to gamma radiation.

The optical fiber of the radiation detector 110 may configured to optically couple the scintillation material with a photodetector, such as a photodiode. That is, scintillation photons generated by the scintillation material (e.g., in response to absorbing gamma rays) may be coupled by the optical fiber to a photodetector. In turn, the photodetector may provide a signal (e.g., a photovoltage) based on the number of absorbed scintillation photons.

In an example embodiment, the photodetector may include a photomultiplier tube (PMT), a charge-coupled device (CCD), an avalanche photodiode (APD), or another type of optical amplifier or detector configured to convert photons into photoelectrons. In such a scenario, the photoelectrons may provide measurable electrical pulse and/or signal. In the case in which the emission light from the scintillation material is 611 nm, the photodetector may be configured to absorb photons at 611 nm.

Other types of radiation detectors are possible. For example, gas ionization, semiconductor, solid scintillator or liquid scintillator detectors may be possible within the context of the present disclosure. Furthermore, while some embodiments disclosed herein relate to a single radiation detector, multiple radiation detectors are possible. For example, two radiation detectors may be used as a "stereo pair", which may be operable to more accurately determine a location of the radiation source 130. Furthermore, three radiation detectors may be used as a triplet arrangement and provide further radiation source location resolution and/or other capabilities. For example, using multiple radiation detectors may enable three-dimensional radiation dose mapping. Radiation detector arrays are also possible.

In an example embodiment, the radiation detector 110 may be operable to provide data to the controller at a 50 Hz rate, although higher data rates (e.g., kHz rates) are possible.

The controller 120 may include one or more processors 122 and a memory 424. The memory 124 may include instructions 126 and/or an expected dose profile 128. The instructions 126 may be executed by the processor(s) 122 so as to carry out various operations described herein. The controller 120 may be implemented in various forms. For example, the controller 120 may be standalone unit (e.g., a laptop, a desktop computer, or a mobile device). Additionally or alternatively, the controller 120 may be incorporated into the remote afterloader 170. In general, the controller 120 may be configured to execute instructions so as to carry out operations.

Such operations may include receiving, from the radiation detector 110, real-time information indicative of at least one of: a particle flux rate, an energy fluence, or an absorbed dose of ionizing radiation emitted from the radiation source 130. The operations may also include determining, based on the received information, at least one of: a location of the radiation source 130 or a dwell time of the radiation source 130.

Optionally, the operations may include determining a measured dose profile based on the received information. In such a scenario, the measured dose profile may include a plurality of measured dose values. Furthermore, each measured dose value of the plurality of measured dose values may be associated with a respective time.

In an example embodiment, the operations may include determining a safety interlock condition based on a difference between the measured dose profile and an expected dose profile. The expected dose profile includes a plurality of expected dose values and each expected dose value of the plurality of expected dose values may be associated with a respective time. In another embodiment, the safety interlock condition may be determined based on a difference between a measured dose rate and an expected dose rate. In yet another embodiment, the safety interlock condition may be determined based on a difference between a measured radiation fluence and an expected radiation fluence.

In the scenario where the controller determines the safety interlock condition, the controller may cause a safety interlock to reduce or eliminate the ionizing radiation received by the radiotherapy target. That is the safety interlock may include a way to retract the radiation source 130 from the applicator 160 and/or the patient.

According to example embodiments herein, the controller 120 may be operable to control and/or adjust parameters associated with one or more of the other elements of system 100. For example, the controller 120 may control or adjust a parameter of the radiation detector 110 (e.g., gain setting). Additionally, the controller 120 may be operable to control the display 140, safety interlock 150, or at least some functions of the remote afterloader 170.

As an example, the operations of the controller may include causing a remote afterloader 170 to load the radiation source 130 into a loading end of an applicator 160. The operations may further include moving the radiation source 130 along the applicator 160 via a plurality of predetermined dwell positions. The applicator 160 may include the loading end and a treating end, which may be disposed proximate to the radiotherapy target. Upon arrival at each predetermined dwell position, the radiation source 130 may remain stationary for a respective dwell time.

The expected dose profile 128 may include information about an expected signal from the radiation detector 110 for a given brachytherapy treatment procedure. Among other factors, the expected dose profile 128 may be based on a proposed placement of the applicator 160, the proposed location or other characteristics of the radiation detector 110, the location of the radiotherapy target, characteristics of the radiation source 130, and characteristics of the patient.

In an example embodiment, the radiation source 130 may include an Iridium-192. In such a scenario, the radiation source 130 may emit y rays. However other radioactive sources are contemplated. For example, the radiation source 130 may include various radioisotopes of cesium, cobalt, iodine, palladium, ruthenium, and/or radium. The radiation source 130 may include a "needle" of about 1 millimeter in diameter, or smaller. Additionally or alternatively, the radiation source 130 may have a larger diameter.

Radiation doses may be quantified in terms of a gray (Gy), which is equivalent to absorbing one joule of radiation energy per kilogram of matter. In embodiments disclosed herein, a variety of doses and dose rates are possible. As an example, systems and methods herein may be operable to conduct high-dose rate (HDR) brachytherapy, which may include a dose rate of greater than 12 gy/hour. HDR brachytherapy may be used to treat cancers of the breast, prostate, lungs, esophagus, and cervix, among others. Systems and methods herein may additionally or alternatively enable Low-dose rate (LDR), Medium-dose rate (MDR), and/or Pulsed-dose rate (PDR) brachytherapy procedures. Furthermore, systems and methods described herein may be applied to temporary and/or permanent brachytherapy treatments.

The one or more displays 140 may include a touch screen, a video screen, monitor, a heads-up display, or another type of display operable to show graphics and/or text for viewing. In an example embodiment, the display 140 may be configured to display the expected dose profile as well as a real-time dose profile during the brachytherapy procedure. In another embodiment, the display 140 may be integrated into a mobile device. Optionally, the display 140 may be operable to provide a graphical and/or audio alarm to a user of the system 100. Other types of user interface feedback are possible.

The safety interlock 150 may include a device configured to reduce or stop radiation emitted from the radiation source 130. Additionally or alternatively, the safety interlock 150 may include a visual and/or audio alarm signal. As a further alternative, the safety interlock 150 may include a communication interface with the remote afterloader 170. Namely, the safety interlock 150 may provide a signal path between the controller 120 and the remote afterloader 170. In the scenario where a measured detector signal differs from the expected detector signal more than a threshold amount, the controller 120 may send a signal to the remote afterloader 170 via the safety interlock 150. As such, the remote afterloader 170 may withdraw the radiation source 130 from the applicator 160 and store the radiation source 130 in a radiation-proof vault. Additionally or alternatively, the remote afterloader 170 may withdraw the applicator 160 from the patient in response to receiving notification of a safety interlock condition.

The applicator 160 may include a plastic catheter and/or a needle formed from a non-radioactive material. The applicator 160 may be arranged as a hollow tube, a cylindrical stub, or another shape. The applicator 160 may include one or more dwell locations. The dwell locations may provide a fixed or known geometry of locations at which the radiation source 130 may dwell for respective dwell times. In an example embodiment, the applicator 160 may include a plurality of dwell locations. In such a scenario, the remote afterloader 170 may be configured to move the radiation source 130 between respective dwell locations of the applicator 160.

A variety of different combinations of radiation detectors 110, radiation sources 130, and applicator 160 are possible with the scope of this disclosure. For example, a plurality of radiation sources 130 may be used in the brachytherapy procedure.

At least a portion of the radiation detector 110 may be configured to be biocompatible with human patients. As such, the radiation detector 110, or at least the optical fiber may be at least partially biocompatible so as to be positioned in a patient.

The remote afterloader 170 may provide an alternative to manual loading of radioactive sources, particular in the case of HDR brachytherapy. The remote afterloader 170 may include a device configured to deliver one or more radiation sources 130 to one or more dwell positions in the applicator 160 via one or more source guide tubes. In an example embodiment, the remote afterloader 170 may utilize a variety of methods to transfer the radiation source 130 to the applicator 160. Specifically, the remote afterloader 170 may utilize ball-chains, steel guide wires, helical steel springs, and/or pneumatic mechanisms to move the radiation source 130 to specific locations in the applicator 106.

The remote afterloader 170 may also include one or more ways to retract the radiation source 130 in the event of an emergency or power failure. For example, the remote afterloader 170 may have a battery back-up or manual crank mechanism. The remote afterloader 170 may also include a source storage, which may be configured to house the radiation sources 130 when not in use. In some embodiments, the remote afterloader 170 may include a plurality of applicator "channels". That is, the remote afterloader 170 may be operable to deliver multiple radiation sources 130 to multiple dwell locations on the applicator 160, or to dwell locations on multiple applicators.

Figure 2A:
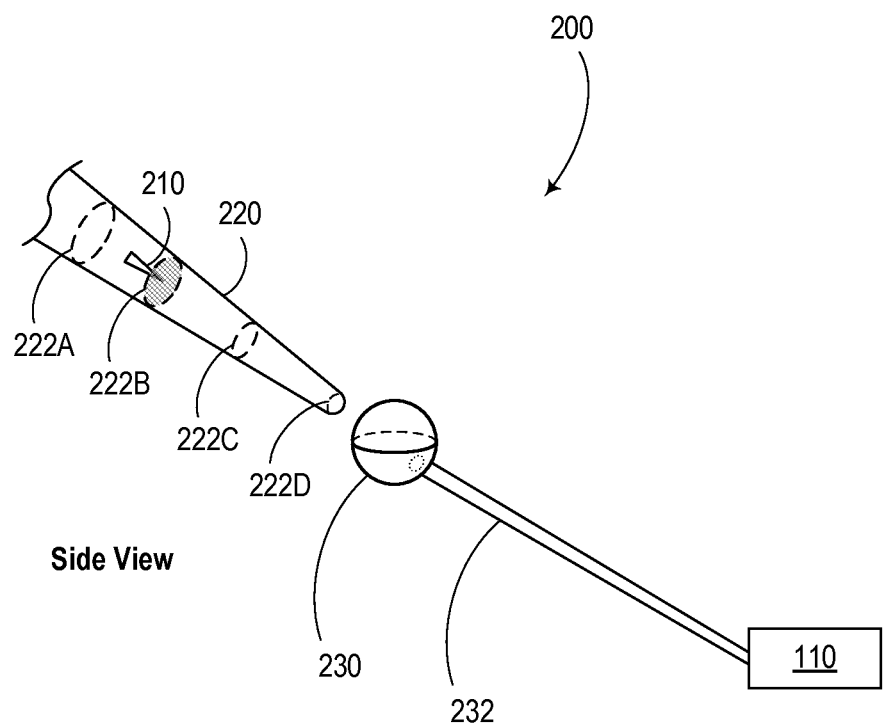
FIG. 2A illustrates a system, according to an example embodiment.
Figure 2B:
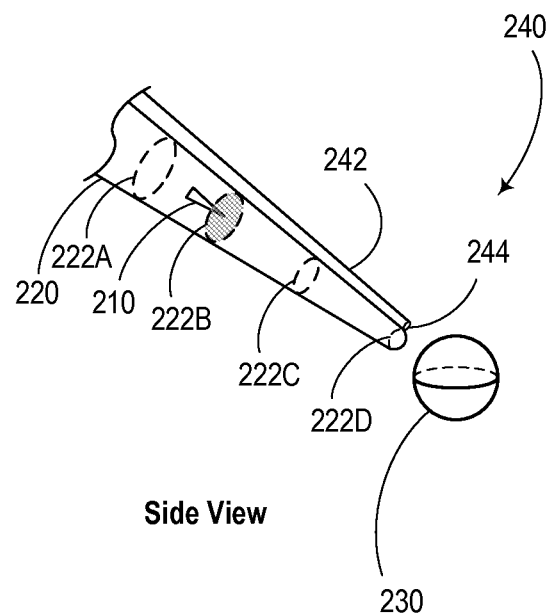
FIG. 2B illustrates a system, according to an example embodiment.
Figure 2C:
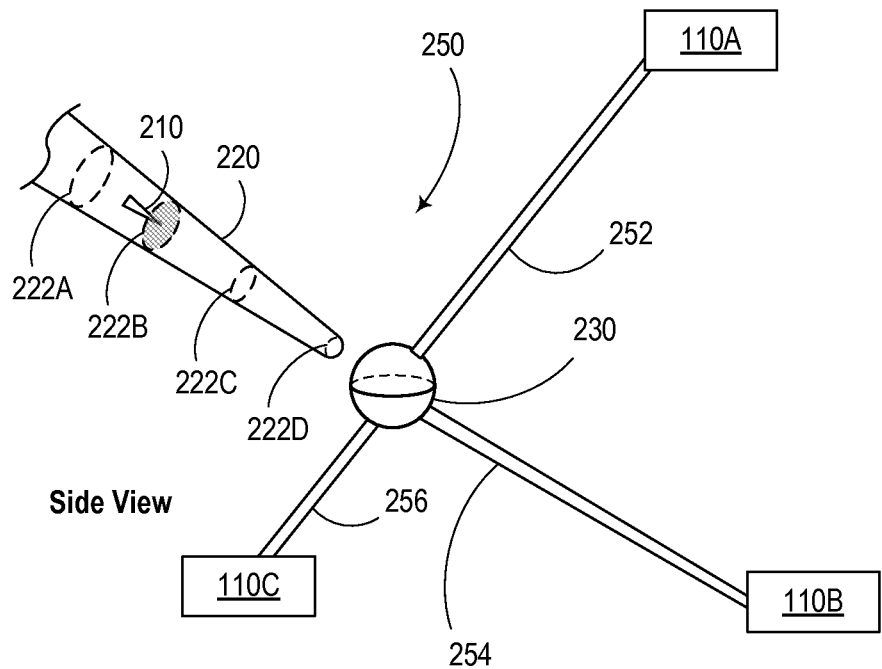
FIG. 2C illustrates a system, according to an example embodiment.

FIGS. 2A, 2B, and 2C may illustrate systems according to embodiments that may involve different arrangements of the applicator and radiation detector with respect to a radiotherapy target. FIGS. 2A, 2B, and 2C may include elements that are similar or identical to corresponding elements in system 100 as illustrated and described in relation to FIG. 1.

FIG. 2A illustrates a system 200, according to an example embodiment. System 200 may include a radiation source 210 located within an applicator 220. The applicator 220 may include a plurality of dwell locations 222A, 222B, 222C, and 222D. As illustrated, radiation source 210 may be located proximate to dwell location 222B. However, it is understood that the radiation source 210 may be moved to any of the plurality of dwell locations 222A-D. Alternatively or additionally, the radiation source 210 may be withdrawn from the applicator 220. For example, the radiation source 210 may be housed in a radiation-proof vault when not in use.

The applicator may be positioned proximate to a radiotherapy target 230. In an example embodiment, the radiotherapy target 230 may include tissue having precancerous and/or cancerous cells (e.g., a tumor). Furthermore, an optical fiber 232 of the radiation detector 110 may be positioned proximate to the radiotherapy target 230. As illustrated, the optical fiber 232 may be positioned such that radiation from the radiation source 210 may pass substantially through the radiotherapy target 230 before reaching scintillation material coupled to the end of the optical fiber. In other words, the optical fiber 232 and the applicator 220 may be arranged substantially coaxially in a "transmission" geometry with the radiotherapy target 230 (e.g., the tumor).

In some embodiments, the applicator 220 and/or the radiation source 210 may be positioned inside the radiotherapy target 230.

FIG. 2B illustrates a system 240, according to an example embodiment. System 240 may include an applicator 220 and a radiation source 210 that are similar or identical to those in system 200. Similar to FIG. 2A, the applicator 220 may be proximate to the radiotherapy target 230. In an example embodiment, an optical fiber 242 may be coupled to the applicator 220. In other words, the optical fiber 242 and the applicator 220 may be arranged substantially coaxially in a "backscatter" geometry with the radiotherapy target 230. Other configurations of the optical fiber 242 and the applicator 220 are possible.

FIG. 2C illustrates a system 250, according to an example embodiment. The system 250 may include an applicator 220 and a radiation source 210 that are similar or identical to those in system 240 and system 200 as illustrated and described in reference to FIGS. 2A and 2B. In an example embodiment, three radiation detectors 110A, 110B, and 110C may have respective optical fibers 252, 254, and 256 that are positioned proximate to the radiotherapy target 230. In such a scenario, utilizing information from three radiation detectors 110A, 110B, and 110C may provide higher resolution, better accuracy, and/or better reliability than using a single radiation detector. In some embodiments, multiple radiation detectors may provide information so as to generate a two-dimensional and/or a three-dimensional radiation dose map.

Figure 3:
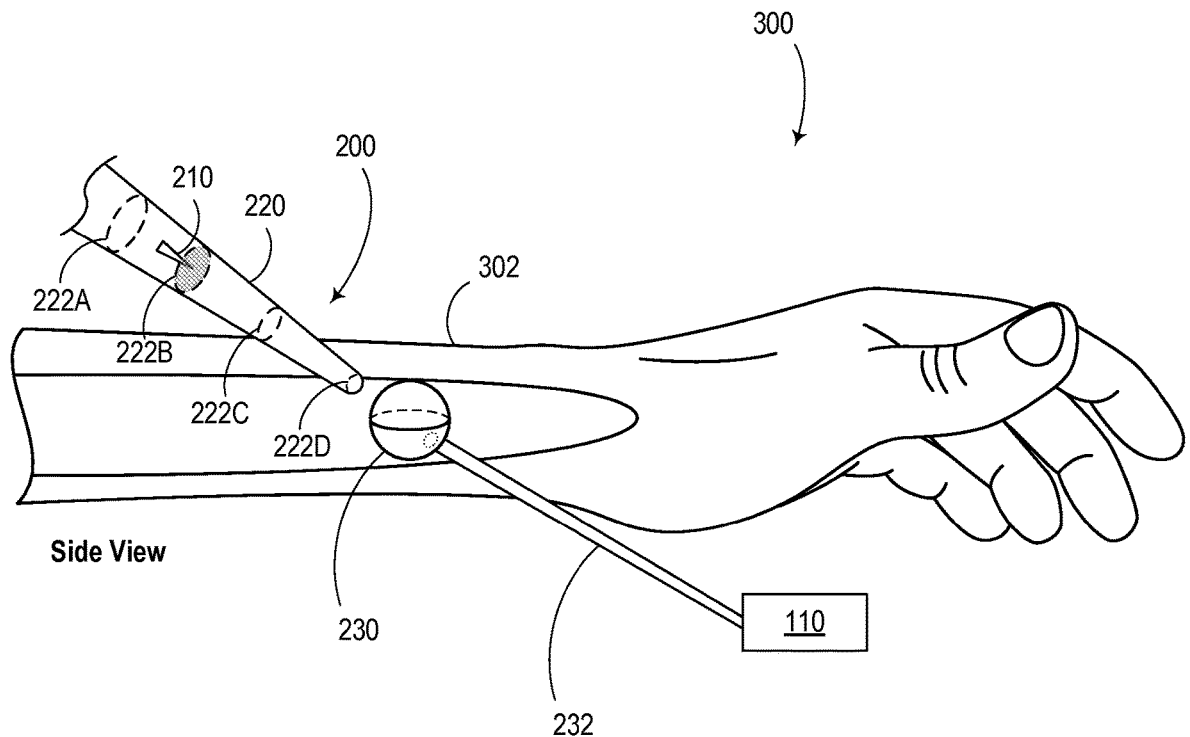
FIG. 3 illustrates a system, according to an example embodiment.

FIG. 3 illustrates a system 300, according to an example embodiment. System 300 may include elements that may be similar or identical to corresponding elements illustrated and described in reference to FIGS. 1, 2A, 2B, and 2C. In an example embodiment, some of the elements of system 300 may be positioned adjacent to, or inside, human tissue. For example, as illustrated in FIG. 3, the radiotherapy target 230 may be located under a skin surface 302. As such, at least a portion of one or both of the applicator 220 and/or the optical fiber 232 of radiation detector 110 may be positioned in vivo. Additionally or alternatively, the applicator 220 and/or the optical fiber 232 may be positioned adjacent to, and outside of, the skin surface 302. It is understood that radiotherapy targets may be located in a variety of other locations inside of, and on the surface of, the human body. Accordingly, applicator 220 and/or the optical fiber 232 may be positioned, shaped, and/or configured in various ways so as to provide efficient and accurate delivery of, and detection of, a radiation dose to the radiotherapy target 230.

Figure 4A:
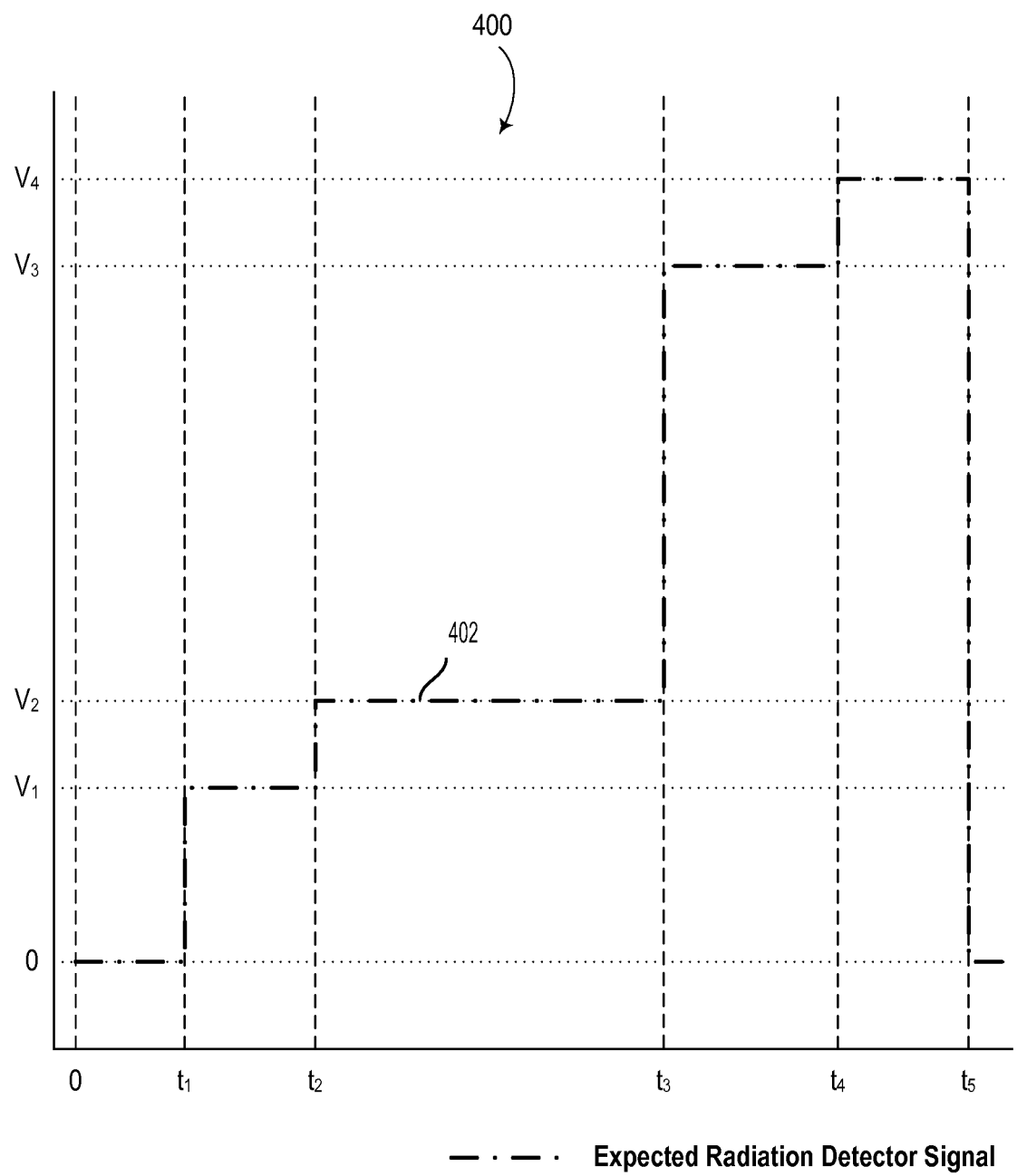
FIG. 4A is a graph of an expected radiation detector signal, according to an example embodiment.

FIG. 4A is a graph 400 of an expected radiation detector signal 402 versus time, according to an example embodiment. The expected radiation detector signal 402 versus time may be obtained in various ways. For example, the expected radiation detector signal 402 may be calculated from theory, estimated from empirical data, or obtained via experimentation with phantoms. In an example embodiment, a radiation detector, such as radiation detector 110, may be placed proximate to a phantom configured to be shaped like or absorb radiation like a part of the anatomy that contains a radiotherapy target. In such a scenario, an applicator, such as applicator 160, may be positioned in an anatomically correct location in or near the phantom. While a radiation source is moved into various dwell positions in the applicator, the radiation detector may measure characteristics of radiation dose exposure in a real-time manner.

With reference to FIGS. 2A, 2B, and 2C, expected radiation detector signal 402 may represent an actual signal detected with a phantom while the radiation source is moved between dwell positions by a remote autoloader. Specifically, expected radiation detector signal 402 may be zero while the radiation source is within a radiation-proof vault of the autoloader system (e.g., between t=0 and t=$t_1$).

At $t_1$, the remote autoloader may cause the radiation source (e.g., radiation source 210) to move to dwell position 222A. The radiation source may dwell at dwell position 222A for $t_2$–$t_1$. While dwelling at dwell position 222A, the radiation detector may be expected to provide a signal voltage equal to $V_1$.

At t=$t_2$, the remote autoloader may cause the radiation source to move to dwell position 222B. The radiation source may dwell at dwell position 222B for $t_3$–$t_2$. In such a scenario, the radiation detector may detect a higher radiation exposure, and thus provide a higher signal voltage, $V_2$.

At $t_3$, the remote autoloader may cause the radiation source to move to dwell position 222C. The radiation source may dwell at dwell position 222C for $t_4$–$t_3$. While dwelling at dwell position 222C, the radiation detector may be expected to provide a signal voltage equal to $V_3$.

At $t=t_4$, the remote autoloader may cause the radiation source to move to dwell position 222D. The radiation source may dwell at dwell position 222D for $t_5-t_4$. In such a scenario, the radiation detector may detect a yet higher radiation exposure, and thus provide a higher signal voltage, $V_4$.

At $t=t_5$, the remote autoloader may retract the radiation source out of the applicator and replace it in a radiation-proof vault, which may be part of the autoloader system. As such, the radiation detector signal may drop to zero.

Figure 4B:
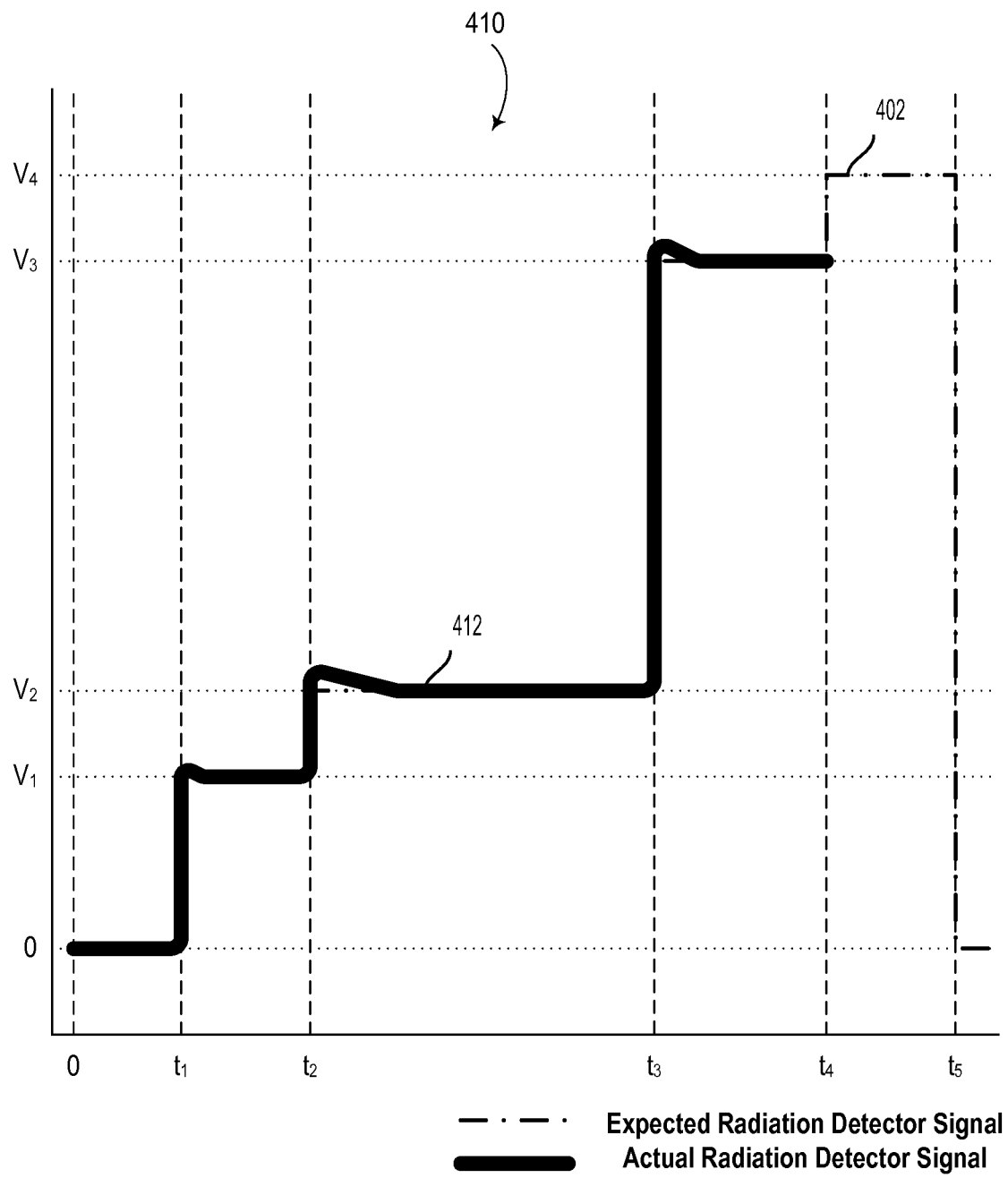
FIG. 4B is a graph of actual and expected radiation detector signals, according to an example embodiment.

FIG. 4B is a graph 410 of an actual radiation detector signal 412 and an expected radiation detector signal 402, according to an example embodiment. As illustrated in FIG. 4B, the actual radiation detector signal 412 may deviate slightly from the expected radiation detector signal 402. Possible causes of the deviations between the expected and actual detector signals may include, but are not limited to, placement error of the radiation source within the dwell positions in the applicator, mechanical "overshoot", and/or physical differences between the phantom and patient tissues.

As illustrated in FIG. 4B, the actual radiation detector signal 412 may be overlaid on the expected radiation detector signal 402. Such signals may be presented to a user in a user interface and/or a display. In such a scenario, an operator of the system may be able to more easily observe differences between the expected and actual signal levels.

Figure 4C:
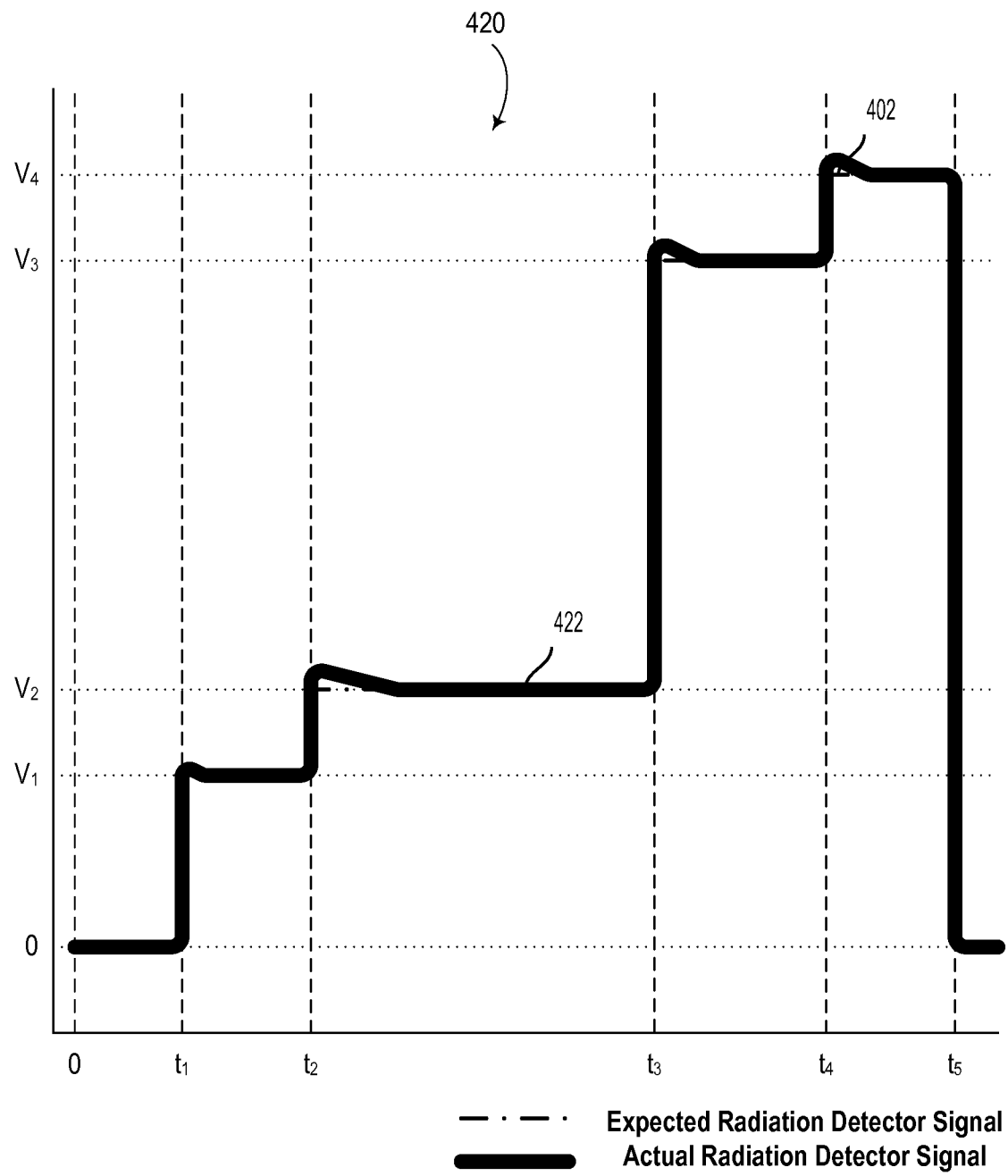
FIG. 4C is a graph of actual and expected radiation detector signals, according to an example embodiment.

FIG. 4C is a graph 420 of actual radiation detector signal 422 and the expected radiation detector signal 402, according to an example embodiment.

Figure 5A:
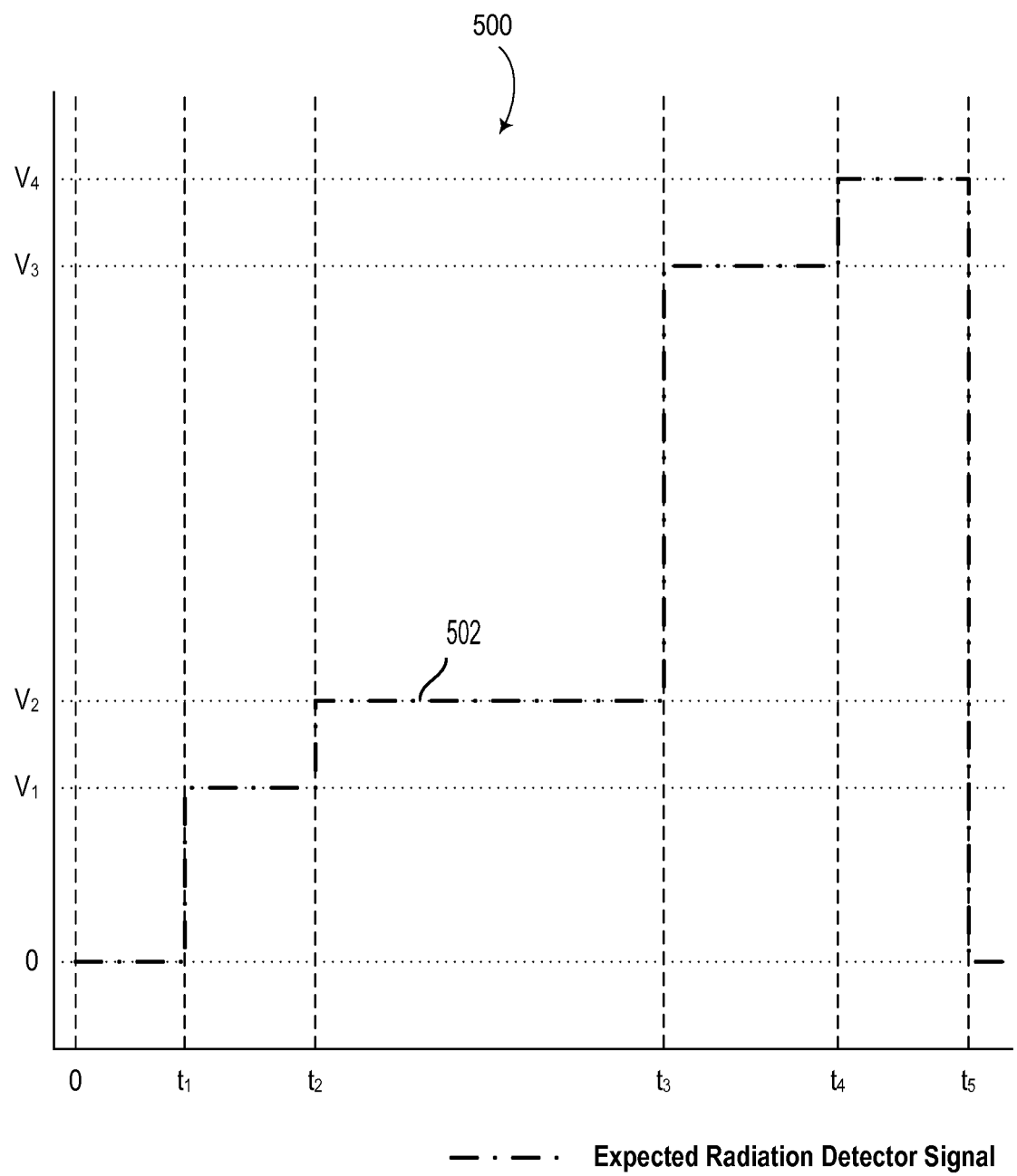
FIG. 5A is a graph of an expected radiation detector signal, according to an example embodiment.

FIG. 5A is a graph 500 of an expected radiation detector signal 502, according to an example embodiment. The expected radiation detector signal 502 may be similar or identical to the expected radiation detector signal 402 as illustrated and described in reference to FIG. 4A.

Figure 5B:
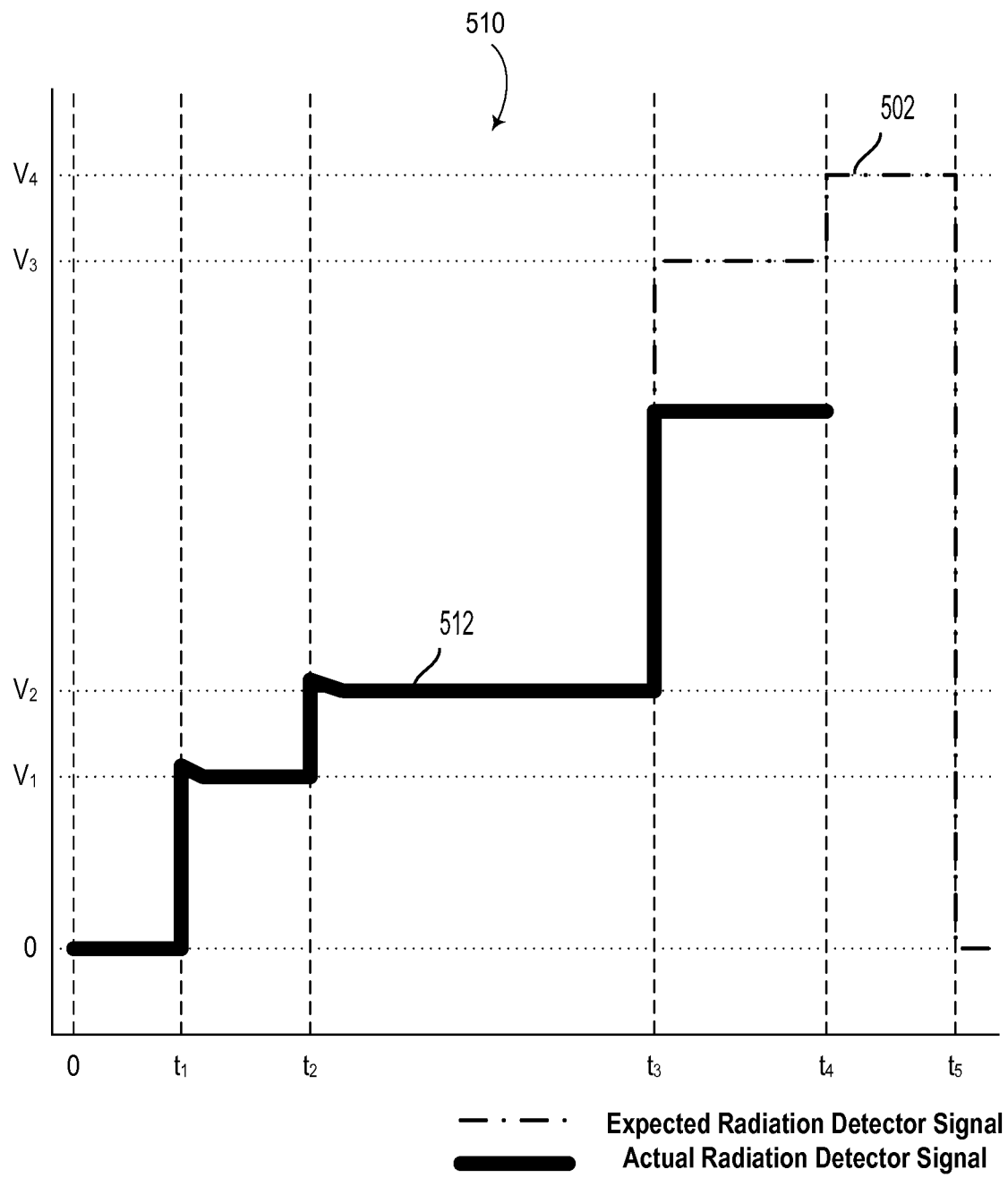
FIG. 5B is a graph of actual and expected radiation detector signals, according to an example embodiment.

FIG. 5B is a graph 510 of an actual radiation detector signal 512 and an expected radiation detector signal 502, according to an example embodiment. The actual radiation detector signal 512 may be a real-time continuous log of the voltage output from a radiation detector, such as radiation detector 110 as illustrated and described in reference to FIG. 1. In some embodiments, the actual radiation detector signal 512 may differ from the expected radiation detector signal 502. For example, as described elsewhere herein, the radiation source and/or the applicator may be incorrectly positioned. In other embodiments, the actual and expected radiation detector signals may differ due to a movement of the optical fiber coupled to the radiation detector. As illustrated in FIG. 5B, the actual radiation detector signal 512 may be less than the expected radiation detector signal 502 beginning at $t=t_3$.

Figure 5C:
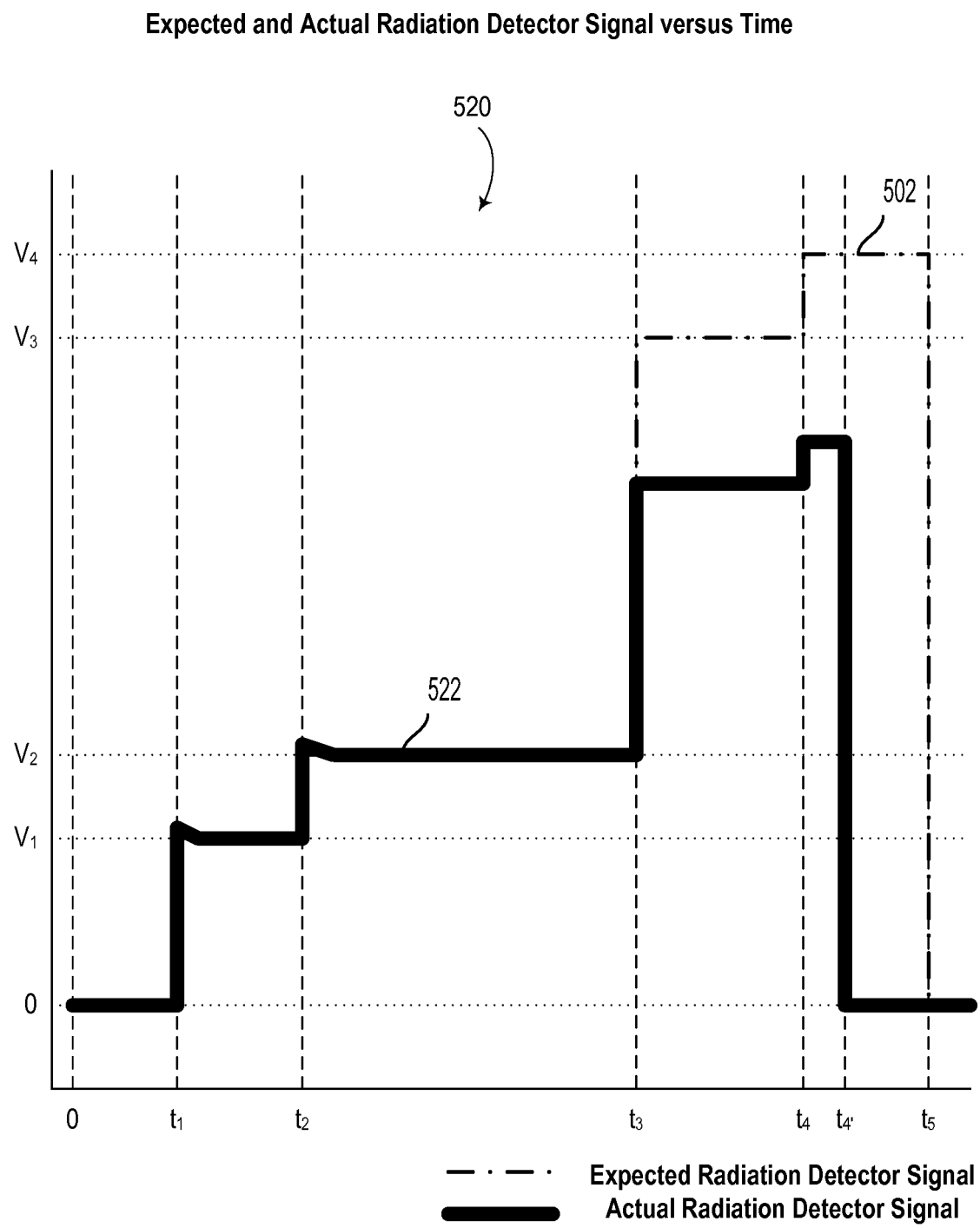
FIG. 5C is a graph of actual and expected radiation detector signals, according to an example embodiment.

FIG. 5C is a graph 520 of an actual radiation detector signal 522 and an expected radiation detector signal 502, according to an example embodiment. Graph 520 may be a continuation of graph 510. Specifically, FIG. 5C may illustrate a scenario in which a safety interlock is triggered. For example, the actual radiation detector signal 522 may differ from the expected radiation detector signal 502 starting at $t=t_3$, and get relatively worse at $t=t_4$. That is, the relative difference between the expected and the actual radiation detector signal may be greater after $t=t_4$.

In an example embodiment, a safety interlock condition may be determined when the actual radiation detector signal 522 differs by more than 20% of the expected radiation detector signal 502. That is, the safety interlock condition may be triggered in cases where the actual radiation detector signal 522 is either less than 80% or more than 120% of the expected radiation detector signal 502. In FIG. 5C as illustrated, the actual radiation detector signal 522 may fall below 80% of the expected radiation detector signal 502. As such, a safety interlock timer may be triggered. The safety interlock timer may be a fixed or variable period of time that the system may wait in the case where the system corrects itself and to avoid intermittent errors or false indications. In some embodiments, the safety interlock timer may be 10 seconds. However, the safety interlock timer may be a different amount of time. Furthermore, the safety interlock timer may be a variable length timer based on the discrepancy between the actual and expected radiation detector signals.

In FIG. 5C, the safety interlock timer may be illustrated as having a length of $t_{4'}-t_4$. In other words, when the controller determines that a safety interlock condition has been triggered, the safety interlock timer may have started counting down. With no change in the difference between the actual and expected radiation detector signals after the safety interlock timer duration, the system may cause a safety interlock. The safety interlock may include a withdrawal of the radiation source from the applicator. As such, the radiation source may be removed from the patient and housed in the radiation-proof vault.

While FIG. 5C may illustrate voltage signal levels, it will be recognized that the safety interlock condition may be triggered by a difference between other types of expected and actual data. For example, while voltage signal levels are described herein, it is understood that other types of signals (e.g. electrical current, optical signals, etc) are possible. Additionally, other types of comparisons may be possible. For instance, the controller may compare an actual real-time dose to an expected dose value. Additionally or alternatively, the controller may compare actual and expected dose rates. Other types of comparisons are possible between expected (or calculated) and measured data.

Method Examples

Figure 6:
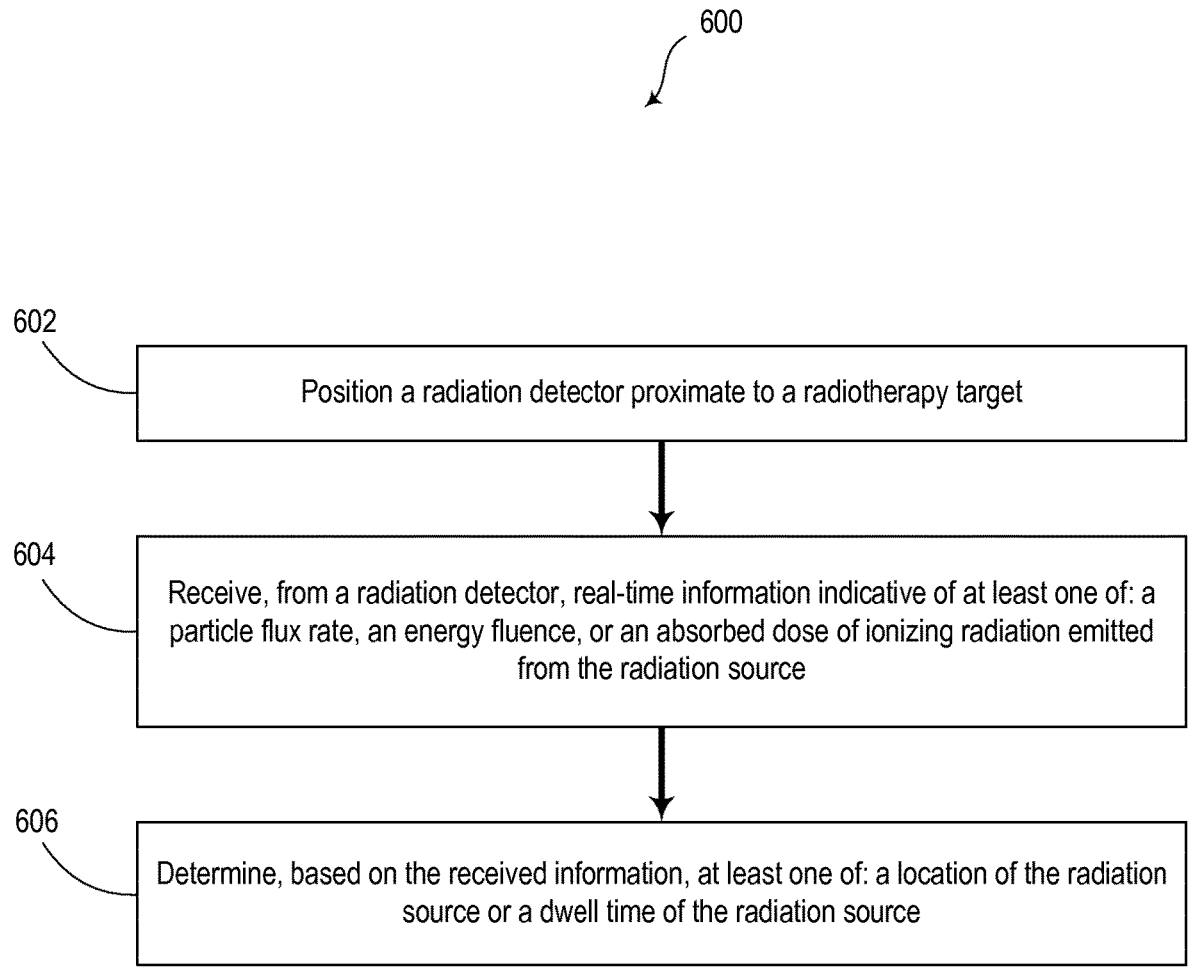
FIG. 6 illustrates a method, according to an example embodiment.

FIG. 6 illustrates a method 600, according to an embodiment. The method 600 includes blocks that may be carried out in any order. Furthermore, various blocks may be added to or subtracted from method 600 within the intended scope of this disclosure. The method 600 may correspond to steps that may be carried out using systems 100, 200, 240, 250, and 300 as illustrated and described in reference to FIGS. 1, 2A, 2B, 2C, and 3.

Block 602 includes positioning a radiation detector proximate to a radiotherapy target.

Block 604 includes receiving, from a radiation detector, real-time information indicative of at least one of: a particle flux rate, an energy fluence, or an absorbed dose of ionizing radiation emitted from the radiation source.

Block 606 includes determining, based on the received information, at least one of: a location of the radiation source or a dwell time of the radiation source.

The method 600 may optionally include a variety of other blocks or steps. For example, the method 600 may include positioning a treating end of an applicator (e.g., applicator 160) proximate to the radiotherapy target (e.g., radiotherapy target 230).

The method 600 may also include loading a radiation source into the loading end of the applicator and moving the radiation source along the applicator via a plurality of predetermined dwell positions. Upon arrival at each predetermined dwell position, the radiation source may remain stationary for a respective dwell time. In some cases, loading the radiation source into the loading end of the applicator may be performed by a remote afterloader.

In an example embodiment, method 600 may include determining a measured dose profile based on the received information from the radiation detector. The measured dose profile includes a plurality of measured dose values, and each measured dose value of the plurality of measured dose values is associated with a respective time.

In a further example, method 600 includes determining a safety interlock condition based on a difference between a measured dose profile and an expected dose profile. As described herein, in response to determining the safety interlock condition, the method 600 may include causing a safety interlock to reduce or eliminate the ionizing radiation received by the radiotherapy target. In other words, the safety interlock may include unloading the radiation source via a loading end of the applicator.

In an example embodiment, method 600 includes displaying a measured dose profile and an expected dose profile via a display. The display may be similar or identical to display 140 illustrated and described in reference to FIG. 1.

Optionally, method 600 may include the radiation detector being a fiber optic scintillation detector.

Figure 7:
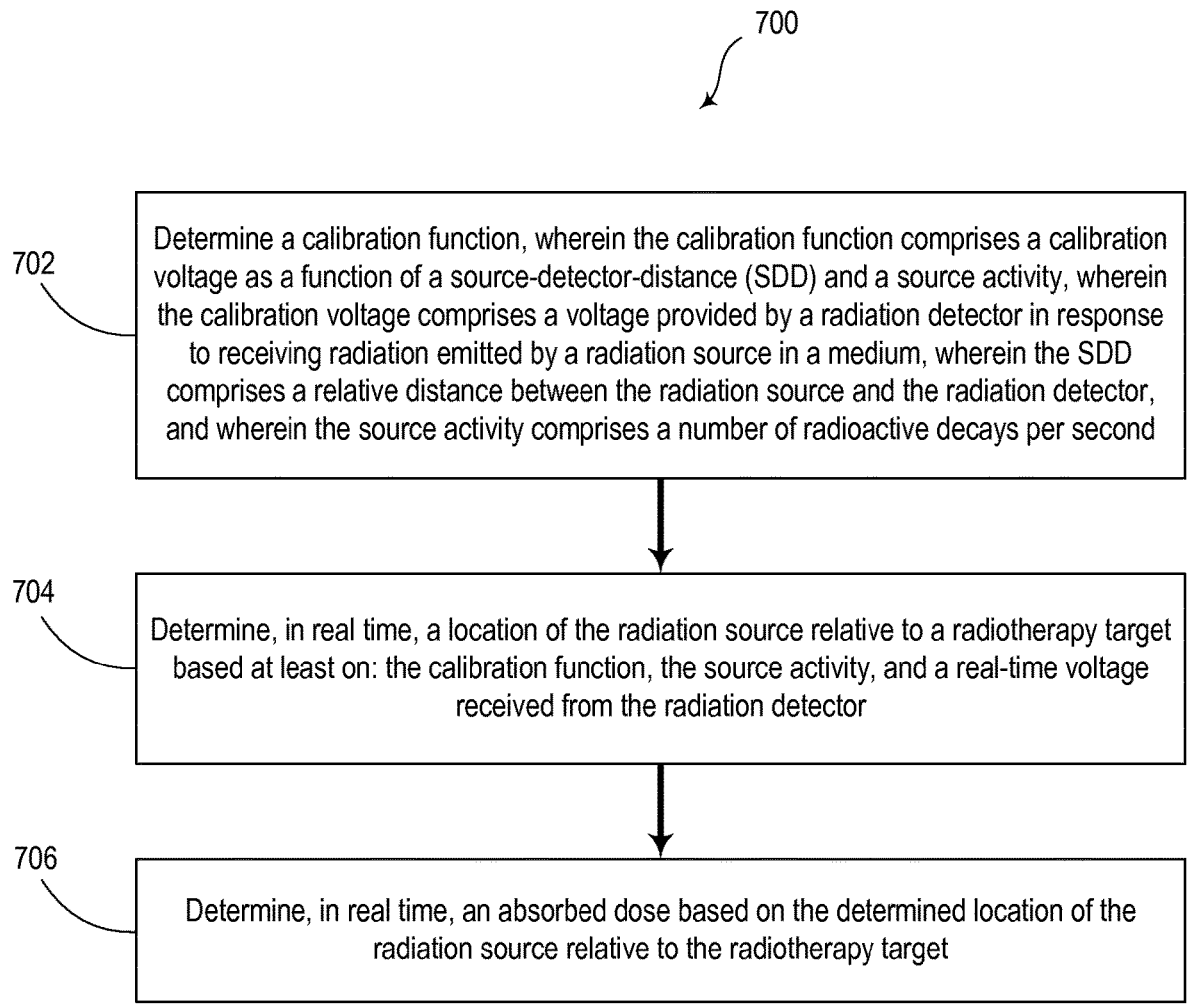
FIG. 7 illustrates a method, according to an example embodiment.

FIG. 7 illustrates a method 700, according to an embodiment. The method 700 includes blocks that may be carried out in any order. Furthermore, various blocks may be added to or subtracted from method 700 within the intended scope of this disclosure. The method 700 may correspond to steps that may be carried out using systems 100, 200, 240, 250, and 300 as illustrated and described in reference to FIGS. 1, 2A, 2B, 2C, and 3. In some embodiments, some or all of the blocks of methods 600 and 700 may be jointly carried out before or while conducting a brachytherapy procedure with a patient.

Method 700 relates to the calibration of a radiation detector for brachytherapy based on knowledge of radioactive source activity. As such, method 700 may be utilized to convert a measured signal received from the radiation detector into a real-time radiation source location and/or a real-time dose value.

Block 702 includes determining a calibration function. The calibration function includes a calibration voltage as a function of a source-detector-distance (SDD) and a source activity. The calibration voltage includes a voltage provided by a radiation detector (e.g., radiation detector 110) in response to receiving radiation emitted by a radiation source in a medium. As an example, a radiation detector may be placed in a medium configured to simulate absorption of radiation in human tissue. For example, the medium may include water and/or a tissue phantom.

The SDD includes a relative distance between the radiation source and the radiation detector. In an example embodiment, determining the calibration function may include measuring a plurality of calibration voltages over a SDD range between 0 and 10 centimeters. That is, in the case that the medium is water, the radiation source (e.g., iridium 192) and the radiation detector may be placed a known distance (SDD) apart from one another. In such a scenario, a controller, such as controller 120 or another computer, may record voltages from the radiation detector as the radiation source is moved within a known relative distance range of 0 and 10 centimeters. In general, the voltage versus relative distance data may resemble a monotonic function with a non-zero slope. It is understood that although voltage signal levels are described herein, other types of signals are possible. For example, the radiation detector may be configured to provide a current signal. Yet further, optical signals are possible. Furthermore, while radiation detectors contemplated herein are described as being coupled to a controller via wires and/or one or more optical fibers, radiation detectors that provide wireless signals to the controller are possible.

In an example embodiment, the calibration function may be expressed as:

$V(t) = f(A \times x(t))$, where $V(t)$ is the detector voltage at a given time, A is the source activity, and $x(t)$ is the relative location of the radiation source from the detector at a given time.

Figure 8:
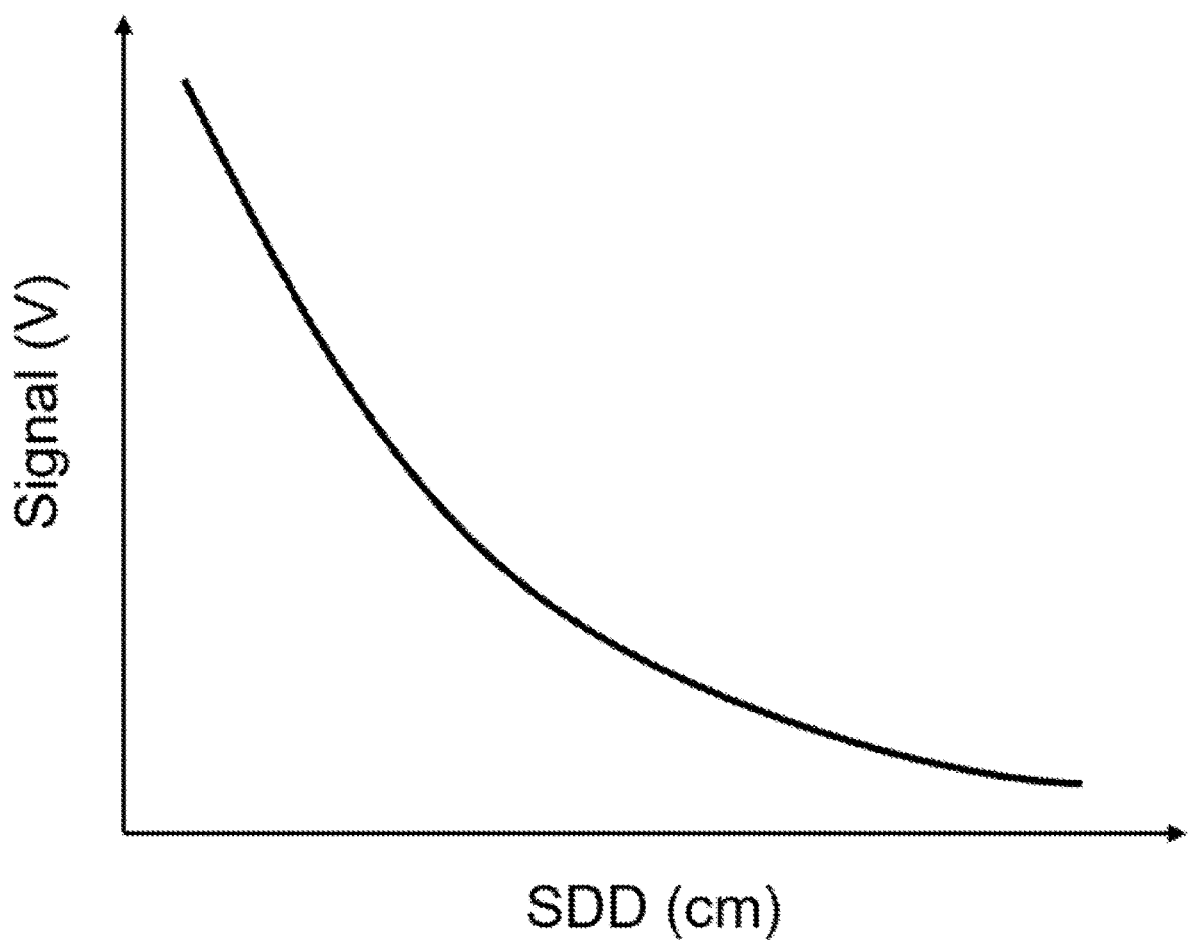
FIG. 8 is a graph showing a sample monotonic function with non-zero slope.

FIG. 8 shows a sample monotonic function 800 with non-zero slope. The sample monotonic function 800 may represent an example calibration voltage curve. In an example embodiment, the calibration voltage curve may decrease exponentially and/or non-linearly over an increasing relative distance between the radiation detector and the radiation source. In such a scenario, each point on the calibration voltage curve includes a unique distance (x) and voltage (y) value. Accordingly, knowledge of the real-time detector signal in volts may provide immediate information about the distance between the radiation source and the radiation detector.

The source activity includes a number of radioactive decays per second. Source activity is based at least on the size and composition of the radiation source. In an example embodiment, the radiation source may be iridium 192 having a diameter of about 1 millimeters and a length of about 3 millimeters. In such a scenario, the source activity may about 10 curies (Ci). Other radiation sources, source sizes, and corresponding source activities are possible.

The detector signal will scale proportionally with source activity. That is, the calibration voltage curve will shift vertically based on the source activity of a given radiation source.

Figure 9:
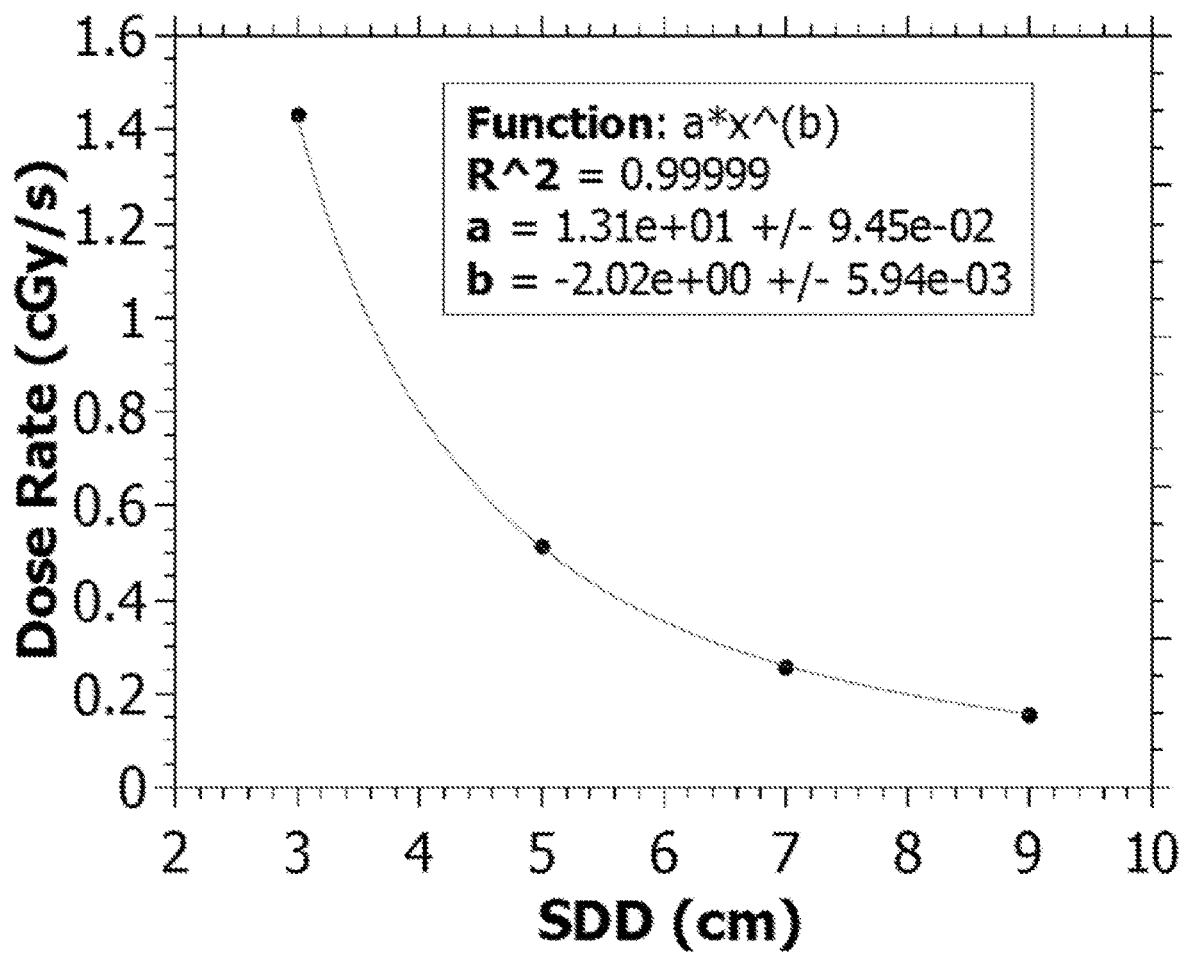
FIG. 9 is a graph showing dose rate as a function of radial distance from a radiation source.

For a radiation source with a known source activity, a dose rate may be calculated versus distance in a given medium. As an example, FIG. 9 is a graph 900 showing dose rate as a function of radial distance from a known radiation source (e.g., iridium 192 with source activity about 10 Ci).

At least two approximations may be made in determining the calibration function. First, at most distances, the radiation source may be considered a point source. That is, for most 3 millimeter long brachytherapy radioactive sources, the point source geometry approximation may be accurate to within 5% at distances greater than 5 millimeters from the source. Accordingly, radial symmetry may be approximated in most cases. In other words, in an example embodiment, radial distance (e.g., SDD) is the primary parameter that needs to be known in order to estimate the dose rate.

Second, the medium between the radiation source and the radiation detector may be approximately homogeneous. That is, the medium may include materials such as air, water, or soft tissue. The medium may additionally or alternatively include a combination of such materials, which may be approximated as a single material by using a linear combination of the independent material properties of the constituent medium materials. As described herein, the characterization medium (water) may be considered to have characteristics sufficiently similar to tissue environments with respect to conducting brachytherapy procedures. However, calibration steps that utilize human tissue phantoms or other mediums are possible within the context of this disclosure.

Figure 10:
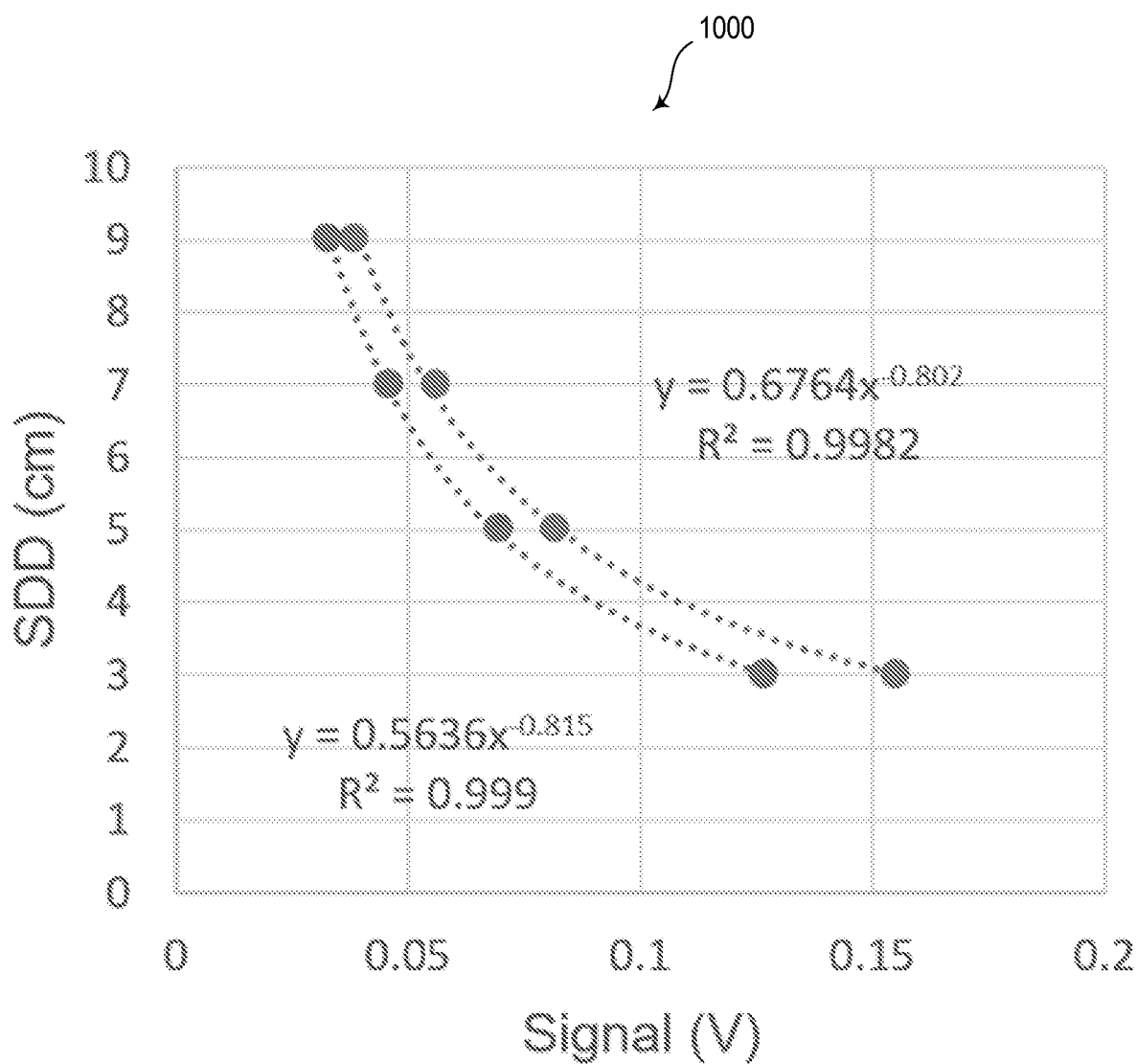
FIG. 10 is a graph showing calibration data from two different radiation detector devices submerged in liquid water medium.

In some embodiments, determining the calibration function may be carried out with multiple radiation detectors and/or radiation sources. For example, FIG. 10 is a graph 1000 showing calibration data from two different radiation detector devices submerged in a liquid water medium. Such information may be utilized to determine a level of uncertainty in the eventual real-time radiation source location and/or the real-time dose rate.

Figure 11:
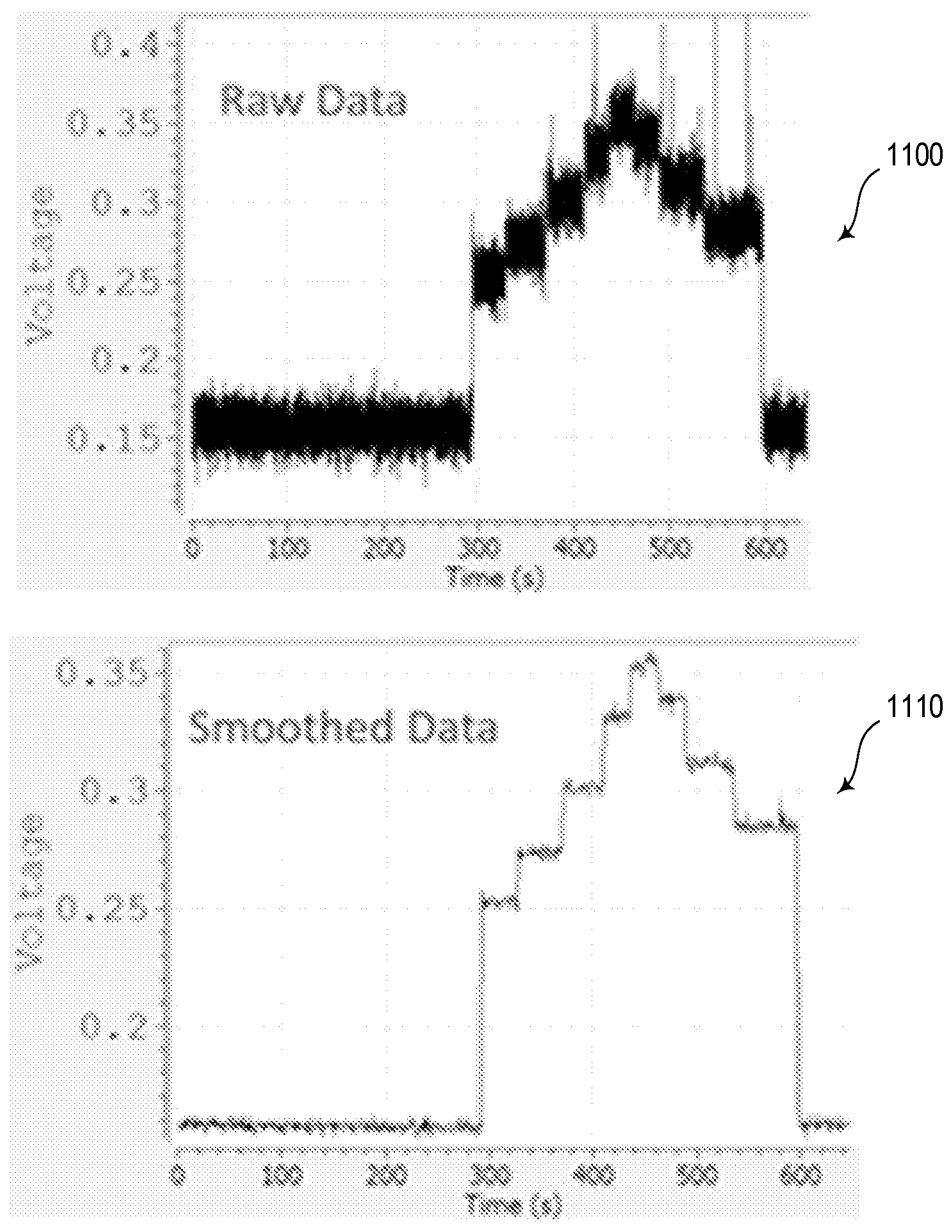
FIG. 11 illustrates graphs showing data acquired during a treatment plan delivered using a vaginal cylinder applicator.

FIG. 11 illustrates graphs 1100 and 1110, which show data acquired during a treatment plan delivered using a vaginal cylinder applicator. Namely, graph 1100 illustrates raw data from the radiation detector as the radiation source is moved into and out of the body with respect to the detector. Furthermore, graph 1110 illustrates smoothed data after a filter or noise reduction process.

In such a scenario, a radiation source was moved to various dwell positions within the vaginal cylinder applicator. During the movement of the radiation source, a radiation detector provided a voltage in response to receiving radiation from the radiation source. The radiation detector was maintained at a known location relative to the radiation source. Based on such real-time radiation detector voltage data, determinations regarding the location of the radiation source and the absorbed dose may be performed, as described below.

Block 704 includes determining, in real time, a location of the radiation source relative to a radiotherapy target based at least on: the calibration function, the source activity, and a real-time voltage received from the radiation detector.

In an example embodiment, the function (f) may be inverted to solve for the relative distance x(t) to the radiation source. That is, the distance x(t) may be expressed as:

$$x(t) = \frac{f^{-1}(V(t))}{A}.$$

Figure 12:
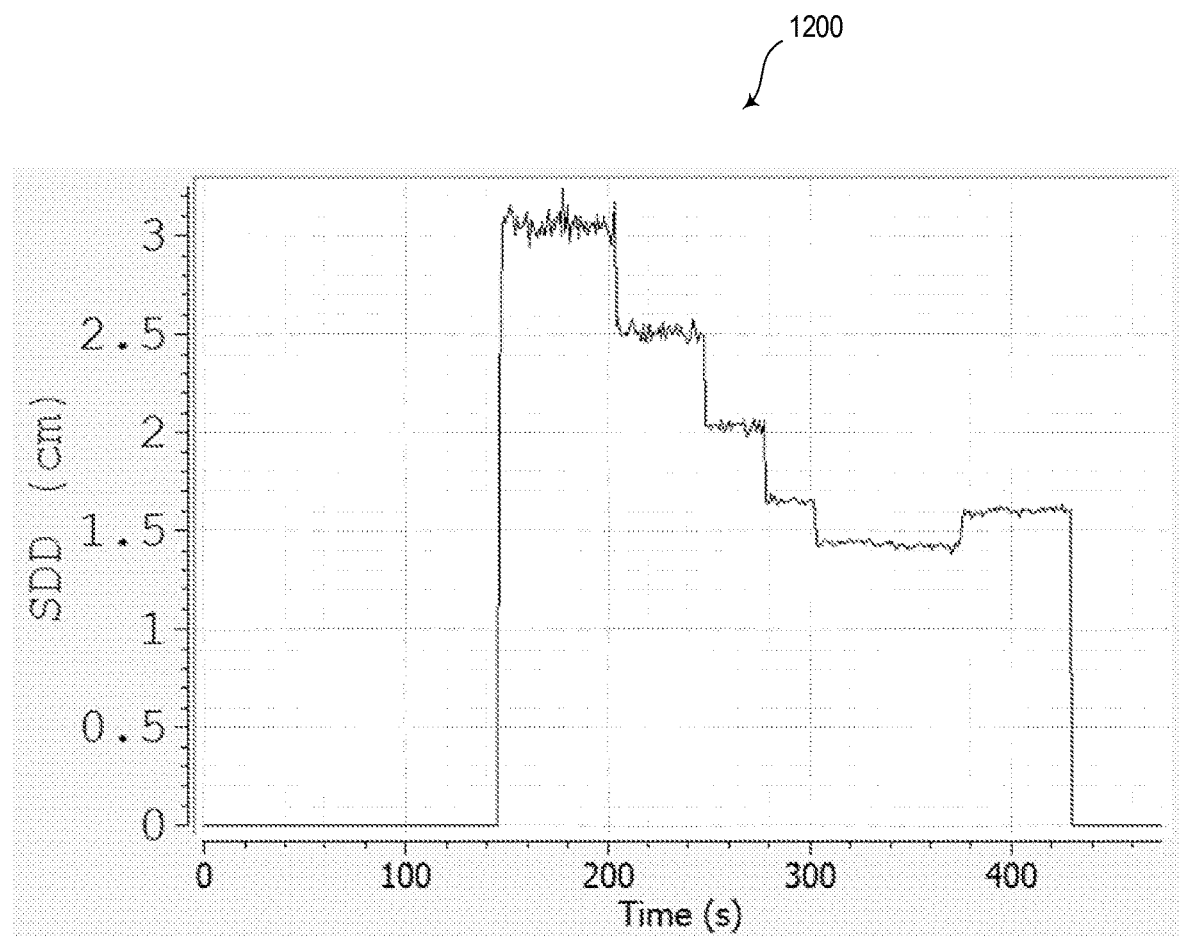
FIG. 12 is a graph showing radiation source location versus time.

Determining the location of the radiation source relative to the radiotherapy target may be performed in real time during a brachytherapy procedure. Furthermore, information indicative of the location of the radiation source relative to the radiotherapy target may be displayed during the brachytherapy procedure via a display for the benefit of medical practitioners. FIG. 12 is a graph 1200 showing an example radiation source location versus time relationship.

Block 706 includes determining, in real time, an absorbed dose based on the determined location of the radiation source relative to the radiotherapy target. That is, a detector signal versus dose curve may be determined by combining the information of the calibration function with the source activity. Such a relationship may be utilized during a brachytherapy procedure to confirm that a measured dose is substantially similar to an expected dose. Furthermore, the dose-rate versus time may be displayed via a display for use by medical practitioners.

In an example embodiment, the distance x(t) may be used to calculate a dose rate, which may be expressed as:

$D_w = g(x(t))$, where $g(x)$ is the dose rate versus radial distance from a known radiation source, such as iridium 192 with a given source activity.

Figure 13:
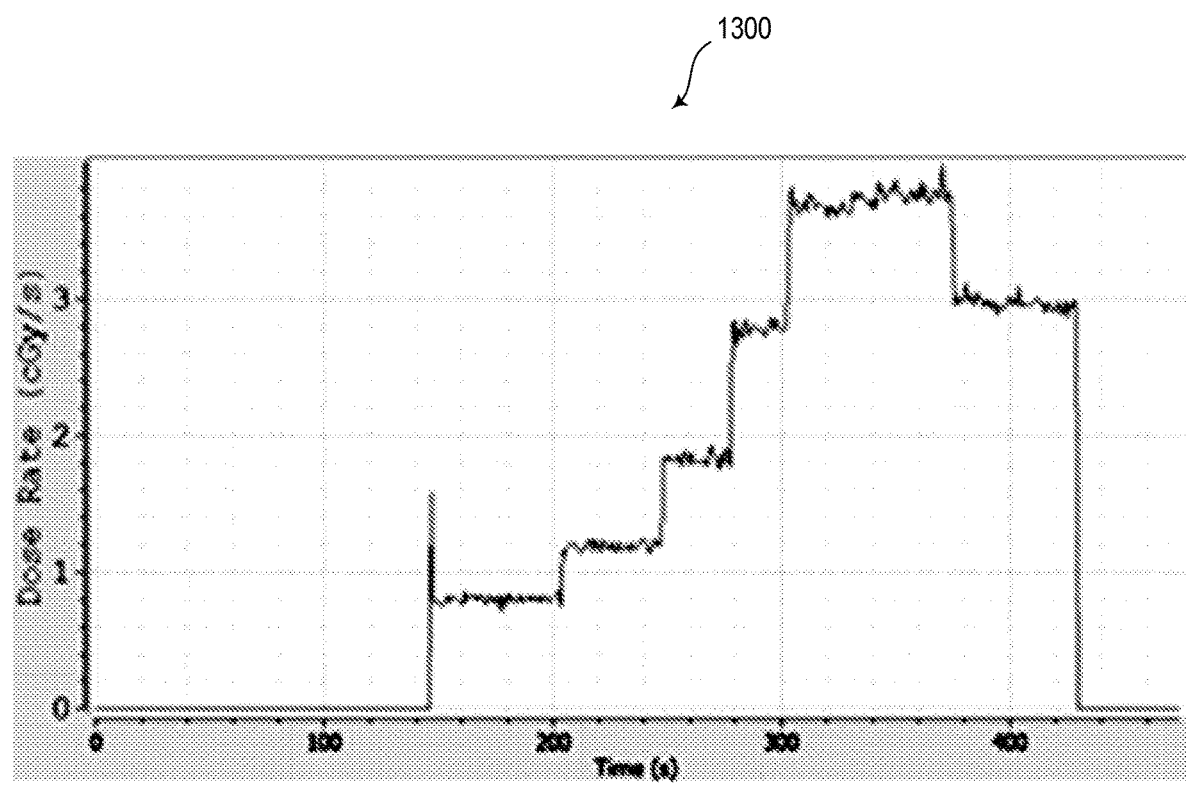
FIG. 13 is a graph showing dose-rate versus time.

FIG. 13 is a graph 1300 showing an example dose-rate versus time relationship.

In some embodiments, methods 600 and 700 may be applied, jointly or individually, to deliver radiation therapy to a patient in need thereof. In such a scenario, the method includes positioning a radiation detector proximate to a radiotherapy target including in vivo tissue. The method also includes receiving, from a radiation detector, real-time information indicative of at least one of: a particle flux rate, an energy fluence, or an absorbed dose of ionizing radiation emitted from the radiation source. The method yet further includes determining, based on the received information, at least one of: a location of the radiation source or a dwell time of the radiation source.

Conclusion

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope and spirit being indicated by the following claims.

What is claimed is:

1. A system comprising:
 a radiation detector configured to be disposed proximate to a radiotherapy target, wherein the radiation detector is configured to provide real-time information indicative of ionizing radiation emitted by a radiation source, wherein the radiation detector comprises a scintillation material, an optical fiber, and a photodetector, wherein the scintillation material is optically coupled to the photodetector via the optical fiber, and wherein a first end of the optical fiber to which the scintillation material is optically coupled is configured to be positionable in a patient proximate to the radiotherapy target while a second end of the optical fiber to which the photodetector is coupled is located outside of the patient; and a controller comprising a memory and a processor, wherein the memory stores instructions that are executable by the processor to cause the controller to perform operations comprising:
receiving, from the radiation detector, real-time information while the radiation source is positioned in the patient and along a plurality of predetermined dwell positions, the real time information being indicative of a particle flux rate, an energy fluence, and an absorbed dose of ionizing radiation emitted from the radiation source; and
determining, based on the received information, a location of the radiation source and a dwell time of the radiation source.

2. The system of claim 1, wherein the operations further comprise determining a measured dose profile based on the received information, wherein the measured dose profile comprises a plurality of measured dose values, wherein each measured dose value of the plurality of measured dose values is associated with a respective time.

3. The system of claim 2, wherein the operations further comprise determining a safety interlock condition based on a difference between the measured dose profile and an expected dose profile, wherein the expected dose profile comprises a plurality of expected dose values, wherein each expected dose value of the plurality of expected dose values is associated with a respective time.

4. The system of claim 3, wherein the operations further comprise, in response to determining the safety interlock condition, causing a safety interlock to reduce or eliminate the ionizing radiation to be received by the radiotherapy target.

5. The system of claim 1, wherein the operations further comprise:
causing a remote afterloader to load the radiation source into a loading end of an applicator; and
moving the radiation source along the applicator via the plurality of predetermined dwell positions, wherein the applicator further comprises a treating end, wherein the treating end of the applicator is disposed proximate to the radiotherapy target, and wherein, upon arrival at each predetermined dwell position of the plurality of predetermined dwell positions, the radiation source remains stationary for a respective dwell time.

6. The system of claim 1, wherein the operations further comprise determining an expected dose profile based on at least one of: a characteristic of the radiation source, a location of the radiotherapy target, or a characteristic of the radiation detector.

7. The system of claim 1, wherein the scintillation material comprises a plastic scintillator.

8. The system of claim 1, wherein at least a portion of the radiation detector is biocompatible, and wherein the biocompatible portion of the radiation detector is configured to be positionable in the patient.

9. The system of claim 1, wherein the scintillation material comprises a cerium-activated glass.

10. The system of claim 1, further comprising a display, wherein the operations further comprise displaying a measured dose profile and an expected dose profile via the display.

11. The system of claim 1, wherein the radiotherapy target comprises in vivo tissue, and wherein the radiation source comprises Iridium-192.

12. The system of claim 11, wherein the in vivo tissue comprises pre-cancerous or cancerous cells.

13. The system of claim 1, wherein the scintillation material comprises an inorganic crystal doped with an activator impurity.

14. The system of claim 1, the operations further comprising:
receiving, from at least one additional radiation detector, additional real-time information and/or three-dimensional dose information.

15. A method comprising:
positioning a scintillation material of a radiation detector proximate to a radiotherapy target, wherein the radiation detector additionally comprises an optical fiber and a photodetector, wherein the scintillation material is optically coupled to the photodetector via the optical fiber, and wherein a first end of the optical fiber to which the scintillation material is optically coupled is configured to be positionable in a patient proximate to the radiotherapy target while a second end of the optical fiber to which the photodetector is coupled is located outside the patient;
receiving, from a radiation detector, real-time information while a radiation source is positioned in the patient and along a plurality of predetermined dwell positions, the real-time information being indicative of a particle flux rate, an energy fluence, and an absorbed dose of ionizing radiation emitted from the radiation source; and
determining, based on the received information, a location of the radiation source and a dwell time of the radiation source.

16. The method of claim 15, further comprising:
positioning a treating end of an applicator proximate to the radiotherapy target, wherein the applicator comprises a loading end and the treating end;
loading the radiation source into the loading end of the applicator; and
moving the radiation source along the applicator via a plurality of predetermined dwell positions, wherein, upon arrival at each predetermined dwell position of the plurality of dwell positions, the radiation source remains stationary for a respective dwell time.

17. The method of claim 16, wherein loading the radiation source into the loading end of the applicator is performed via a remote afterloader.

18. The method of claim 15, further comprising determining a measured dose profile based on the received information, wherein the measured dose profile comprises a plurality of measured dose values, wherein each measured dose value of the plurality of measured dose values is associated with a respective time.

19. The method of claim 18, further comprising determining a safety interlock condition based on a difference between the measured dose profile and an expected dose profile, wherein the expected dose profile comprises a plurality of expected dose values, wherein each expected dose value of the plurality of expected dose values is associated with a respective time.

20. The method of claim 19, further comprising, in response to determining the safety interlock condition, causing a safety interlock to reduce or eliminate ionizing radiation to be received by the radiotherapy target.

21. The method of claim 20, wherein causing the safety interlock to reduce or eliminate the ionizing radiation received by the radiotherapy target comprises unloading the radiation source via the loading end of the applicator.

22. The method of claim 15, further comprising determining an expected dose profile based on at least one of: a characteristic of the radiation source, a location of the radiotherapy target, or a characteristic of the radiation detector.

23. The method of claim 15, further comprising displaying a measured dose profile and an expected dose profile via a display.

24. The method of claim 15, wherein the scintillation material comprises a plastic scintillator.

25. The method of claim 15, wherein the scintillation material comprises a cerium-activated glass.

26. The method of claim 15, wherein the scintillation material comprises an inorganic crystal doped with an activator impurity.

27. The method of claim 15, further comprising:
   receiving, from at least one additional radiation detector, additional real-time information and/or three-dimensional dose information.

* * * * *